United States Patent
Arnold et al.

(10) Patent No.: US 8,605,979 B2
(45) Date of Patent: *Dec. 10, 2013

(54) AUTOMATIC DETECTION AND QUANTIFICATION OF PLAQUE IN THE CORONARY ARTERIES OF SUBJECTS FROM CT SCANS

(75) Inventors: Ben A. Arnold, Columbia, KY (US); Judd E. Reed, Santa Rosa, CA (US)

(73) Assignee: Ben A. Arnold, Columbia, KY (US)

( * ) Notice: Subject to any disclaimer, the term of this patent is extended or adjusted under 35 U.S.C. 154(b) by 142 days.

This patent is subject to a terminal disclaimer.

(21) Appl. No.: 13/118,256

(22) Filed: May 27, 2011

(65) Prior Publication Data

US 2011/0229002 A1 Sep. 22, 2011

Related U.S. Application Data

(63) Continuation of application No. 12/098,425, filed on Apr. 5, 2008, now Pat. No. 7,970,196, which is a continuation of application No. 10/303,663, filed on Nov. 23, 2002, now Pat. No. 7,558,611.

(60) Provisional application No. 60/333,223, filed on Nov. 24, 2001.

(51) Int. Cl.
*G06K 9/00* (2006.01)

(52) U.S. Cl.
USPC ......................................................... 382/131

(58) Field of Classification Search
USPC ........... 382/128, 130, 131; 378/4, 8; 600/426, 600/428
See application file for complete search history.

(56) References Cited

U.S. PATENT DOCUMENTS

| | | | |
|---|---|---|---|
| 4,233,507 A | 11/1980 | Volz | 250/252 |
| 4,649,561 A | 3/1987 | Arnold | 378/207 |
| 4,663,772 A | 5/1987 | Mattson et al. | 378/18 |
| 4,724,110 A | 2/1988 | Arnold | 264/102 |
| 4,782,502 A | 11/1988 | Schulz | 378/18 |
| 4,870,666 A | 9/1989 | Lonn et al. | 378/18 |
| 4,922,915 A | 5/1990 | Arnold et al. | 128/653 R |
| 4,985,906 A | 1/1991 | Arnold | 378/18 |
| 5,034,969 A | 7/1991 | Ozaki | 378/18 |
| 5,068,788 A | 11/1991 | Goodenough et al. | 364/413.14 |
| 5,222,021 A | 6/1993 | Feldman et al. | 364/413.14 |
| 5,235,628 A | 8/1993 | Kalender | 378/207 |
| 5,335,260 A | 8/1994 | Arnold | 378/207 |

(Continued)

OTHER PUBLICATIONS

Agatston, Arthur S. et al. Quantification of coronary artery calcium using ultrafast computed tomography, American College of Cardiology, 1990; 15: pp. 827-832.

(Continued)

*Primary Examiner* — Andrew W Johns
(74) *Attorney, Agent, or Firm* — Jerry Turner Sewell

(57) ABSTRACT

A method automatically detects and quantifies arterial plaque (hard plaque, soft plaque or both) in the coronary arteries of the heart from CT images. The method uses plaque definitions based on subject specific in vivo blood/muscle and fat density measurements, subject specific voxel statistical parameters and 2-D and 3-D voxel connectivity criteria to automatically identify the plaques. The locations of the major arteries are determined in a 3-D coordinate system; and the specific coordinates of the detected plaques are displayed in a plaque map for follow-up exams or ease in plaque review, editing and reporting the results.

22 Claims, 18 Drawing Sheets

(56) References Cited

U.S. PATENT DOCUMENTS

| | | | |
|---|---|---|---|
| 5,442,674 A | 8/1995 | Picard et al. | 378/20 |
| 5,521,955 A | 5/1996 | Gohno et al. | 378/18 |
| 5,577,089 A | 11/1996 | Mazess | 378/54 |
| 5,696,805 A | 12/1997 | Gaborski et al. | 378/54 |
| 5,712,892 A | 1/1998 | Weil et al. | 378/54 |
| 5,757,877 A | 5/1998 | Wilting | 378/8 |
| 5,774,519 A | 6/1998 | Lindstrom et al. | 378/18 |
| 5,782,762 A | 7/1998 | Vining | 600/407 |
| 5,891,030 A | 4/1999 | Johnson et al. | 600/407 |
| 6,026,142 A | 2/2000 | Gueziec et al. | 378/8 |
| 6,226,350 B1 | 5/2001 | Hsieh | 378/98 |
| 6,233,304 B1 | 5/2001 | Hu et al. | 378/8 |
| 6,243,437 B1 | 6/2001 | Hu et al. | 378/8 |
| 6,278,761 B1 | 8/2001 | Kim et al. | 378/8 |
| 6,302,582 B1 | 10/2001 | Nord et al. | 378/207 |
| 6,320,931 B1 | 11/2001 | Arnold | 378/56 |
| 6,421,552 B1 | 7/2002 | Hsieh | 600/425 |
| 6,438,403 B1 | 8/2002 | Cline et al. | 600/410 |
| 6,625,303 B1 | 9/2003 | Young et al. | 382/132 |
| 6,639,965 B1 | 10/2003 | Hsieh et al. | 378/8 |
| 6,674,834 B1 | 1/2004 | Acharya et al. | 378/18 |
| 6,697,451 B2 | 2/2004 | Acharya et al. | 378/18 |
| 6,708,055 B2 | 3/2004 | Geiser et al. | 600/425 |
| 6,789,943 B2 | 9/2004 | Zapalac | 378/207 |
| 6,990,222 B2 | 1/2006 | Arnold | 382/131 |
| 7,127,096 B2 | 10/2006 | Kaufman et al. | 382/131 |
| 7,203,354 B2 | 4/2007 | Wilson et al. | 382/131 |
| 7,251,306 B2 | 7/2007 | Sauer et al. | 378/4 |
| 7,409,035 B2 | 8/2008 | Kaufman et al. | 378/18 |
| 7,471,765 B2 | 12/2008 | Jaffray et al. | 378/65 |
| 7,558,611 B2 | 7/2009 | Arnold et al. | 600/407 |
| 7,583,778 B2 | 9/2009 | Mori | 378/4 |
| 7,970,196 B2 | 6/2011 | Arnold et al. | 382/131 |
| 8,139,836 B2 | 3/2012 | Arnold et al. | 382/131 |
| 2003/0048867 A1 | 3/2003 | Acharya et al. | 378/18 |
| 2003/0095693 A1 | 5/2003 | Kaufman et al. | 382/128 |
| 2003/0120134 A1 | 6/2003 | Rao et al. | 600/300 |
| 2003/0215124 A1* | 11/2003 | Li | 382/131 |
| 2007/0116345 A1 | 5/2007 | Peterson et al. | 382/131 |
| 2008/0273652 A1 | 11/2008 | Arnold et al. | 378/4 |
| 2009/0136107 A1 | 5/2009 | Arnold et al. | 382/131 |
| 2010/0012845 A1 | 1/2010 | Baeumer et al. | 250/361 R |
| 2011/0206247 A1* | 8/2011 | Dachille et al. | 382/128 |

OTHER PUBLICATIONS

Baldy, R.E. et al., A Fully-Automated Computer Assisted Method of CT Brain Scan Analysis for the Measurement of Cerbrospinal Fluid Spaces and Brain Absorption Density, Neuroradiology, vol. 28, 1986, pp. 109-117.

Brown, Matthew S. et al., Knowledge-based segmentation of thoracic computed tomography images for assessment of split lung function, Medical Physics, vol. 27, No. 3, Mar. 2000, pp. 592-598.

Grashuis, J.L. et al., Semi-Automatic Contour Detection in CT-Scans of the Lumbar Spine, Proceedings of the Sixth International Workshop on Bone and Soft Tissue Densitometry, Buxton, England, Sep. 22-25, 1987, p. 33.

Greaser, L.E. 3rd et al., Electron-beam CT: the effect of using a correction function on coronary artery calcium quantitation, Acad. Radiol., vol. 6, No. 1, Jan. 1999, pp. 40-48. (one-page abstract).

Heil, Robert H., Jr., et al., Quantitative Materials Evaluation and Inspection with the Image Analysing Computer, Proceedings of the Society of Photo-Optical Instrumentation Engineers, Feb. 1972, pp. 131-143.

Kachelreiss, Marc et al., ECG-correlated image reconstruction from subsecond multi-slice spiral CT scans of the heart, American Institute of Medical Physics, vol. 27, No. 8, Aug. 2000, pp. 1881-1902.

Kalender, Willi A. et al., Vertebral Bone Mineral Analysis: An Integrated Approach with CT, Radiology, 1987, vol. 164, No. 2, Aug. 1987. pp. 419-423.

Kalender, W.A. et al., Methodological Aspects of Bone Mineral Measurements by QCT: Minimizing Operator Influence on Reproducibility, Proceedings of the Sixth International Workshop on bone and Soft Tissue Densitometry, Buxton, England, Sep. 22-25, 1987, p. 31.

Keller, James M. et al., Automatic Outlining of Regions on CT Scans, Journal of Computer Assisted Tomography, vol. 5, No. 2, Apr. 1981, pp. 240-245.

Kemerink, G.J. et al., Scanner conformity in CT densitometry of the lungs, Radiology, vol. 197, No. 3, Dec. 1995, pp. 749-752. (one-page abstract).

McCullough, Cynthia H., Ph.D., Electron-Beam CT: Use of a Calibration Phantom to Reduce Variability in Calcium Quntitation, Departments of Diagnostic Radiology and Physiology and Biophysics, Mayo Clinic and Mayo Foundation, Rochester, Minnesota, vol. 196, No. 1, Jul. 1995, pp. 159-165.

Reed, Judd E. et al., System for Quantitative Analysis of Coronary Calcification via Electron Beam Computed Tomography, Medical Imaging 1994, Physiological and Function from Multidimensional Images, SPIE, vol. 2168, Feb. 13-14, 1994, pp. 43-53.

Stoel, B.C. et al., Sources of error in lung densitometry with CT, Invest. Radiol., vol. 34, No. 4, Apr. 1999, pp. 303-309. (one-page abstract).

Wankling, P.F. et al., Computer Recognition Applied to C.T. Scans for the Automation of the Procedure for Bone Mineral Measurement Allowing Consistent Measurement Without Operator Intervention, Proceedings of the Sixth International Workshop on Bone and Soft Tissue Densitometry, Buxton, England, Sep. 22-25, 1987, p. 32.

Yoon, H.C. et al., Coronary artery calcium: alternate methods for accurate and reproducible quantitation, Acad. Radiol., vol. 4, No. 10, Oct. 1997, pp. 666-673. (one-page abstract).

General Electric, Marketing Materials distributed in 1987, four pages.

Technical Note, Automatic Outlining Technique for EMI Scanner Pictures, Medical & Biological Engineering & Computing, vol. 17, Sep. 1979, pp. 693-694.

International Search Report dated Oct. 21, 2003, for corresponding International Application No. PCT/US 02/37765 filed Nov. 23, 2002, for Applicant, Image Analysis, Inc., 6 pages.

Zamuner, Umberto, Primary Examiner for the Examining Division of the European Patent Office, "Communication pursuant to Article 94(3) EPC," for corresponding European Patent Application No. 02782371.5, Jul. 1, 2010, 6 pages.

* cited by examiner

AUTOMATIC DETECTION AND QUANTIFICATION OF PLAQUE IN THE CORONARY ARTERIES OF SUBJECTS FROM CT SCANS

RELATED APPLICATIONS

This application is a continuation of U.S. patent application Ser. No. 12/098,425, filed on Apr. 5, 2008, which is a continuation of U.S. patent application Ser. No. 10/303,663, filed on Nov. 23, 2002, which claims priority to U.S. Provisional Patent Application No. 60/333,223, filed Nov. 24, 2001, all of which are incorporated in their entireties by reference herein.

BACKGROUND OF THE INVENTION

1. Field of the Invention

The present invention relates to the field of medical imaging using computed tomography ("CT"), and in particular, to measurements of calcium in the vascular system of a living body.

2. Description of the Related Art

Cardiovascular disease, including heart attacks and strokes, is caused by atherosclerotic plaque build-up from calcification of the arteries of the body, including the coronary arteries, cerebral arteries, renal arteries, etc., and is the leading cause of death in the Western world. Coronary artery disease ("CAD"), the leading cause of death in the United States, is receiving a great amount of attention, particularly with regard to the need for noninvasive, safe, and low-cost tests to diagnose arterial plaque.

Strong correlations have been found between coronary artery calcification and coronary artery occlusions as detected at autopsy. Coronary artery calcium has been shown to be diagnostic of atherosclerotic coronary artery disease. Studies have shown that arterial calcium development is intimately associated with vascular injury and atherosclerotic plaque development. Coronary calcium is present in most patients who suffer acute coronary events. Although many patients with CAD exhibit clinical signs of CAD, including angina or non-fatal myocardial infarction, about half of CAD patients have no symptoms before their sudden deaths.

Advanced atherosclerosis is usually associated with plaque calcification. More than 80% of coronary lesions are calcified, and the presence of calcification is almost certainly associated with plaque. Conversely, the absence of coronary calcium is diagnostic of no coronary lesions with a confidence of 95% to 98%.

While early detection and prevention of atherosclerotic plaque in coronary arteries is desirable, coronary calcium screening is not available in most communities of the U.S. or in the remainder of the world. Conventional noninvasive methods of detection, such as stress tests, are limited by poor performance.

Ultrafast electron beam computed tomography ("EBCT") scanners have shown superior sensitivity for detection and quantification of cardiac calcifications. These scanners allow rapid image acquisition times, which essentially freeze cardiac motion and allow noninvasive measurement of coronary calcifications. More recently, fast, spiral multidetector computed tomography ("MDCT") scanners have been developed with subsecond scan times. Although not as fast as EBCT scanners, MDCT scanners still have scan speeds sufficient to essentially freeze cardiac motion. These scanners are quickly being installed and are increasingly being used for coronary calcium measurements. These scanners generate two-dimensional axial CT images which can be stacked together to produce a three-dimensional image of a volume of the body.

Conventional single-slice computed tomography ("CT") scanners are widely available, being present in almost all U.S. hospitals, even hospitals of small size. These conventional CT scanners have image acquisition times much too long to produce images which freeze cardiac motion, but they are used extensively for imaging the remainder of the body. Current cardiac CT images are acquired with ECG gating, which adds some, although manageable, complexity.

In vitro CT measurements of coronary calcium in cadaver hearts have been compared to later ash weight measurements of calcium content. Estimates of the calcium mass from the CT measurements correlated highly with the actual calcium mass of the ashed specimens (r=0.97). Although the correlation was high, the regression equation relating the actual mass to the mass estimates indicated that the CT mass estimates consistently underestimate actual coronary calcium mass.

SUMMARY OF THE INVENTION

Methods are disclosed which provide automatic location and quantification of arterial calcium in the major arteries of the body. The preferred embodiments disclose methods for coronary and aortic calcium analysis using computerized tomography. The methods preferably use calibrated images for improved precision, but can operate without calibration. The number of interactions by the operator with the images is greatly reduced and in some cases approach zero. The reproducibility of measurements is improved since the operator's subjective judgment is essentially eliminated.

In one preferred embodiment, calcium in the coronary arteries of living patients can be quantified reproducibly by automatic methods. The heart is segmented using preferably calibrated images. The heart is located and its boundaries are identified in 3-D space. In specific patients, it may be necessary for the operator to mark the inferior boundary of the heart to further aid the software in separating heart tissue from liver or sternum. The mode of a histogram analysis of the 3-D segmented heart provides a best measure of the blood/heart tissue density. This value is used to smooth the heart image to remove streak artifacts. The histogram mode is also incorporated into the calibration equation. The aorta is located automatically by using shape, size and density constraints. The aorta is segmented off from the heart and is also used as a beginning location in the search for coronary artery locations.

The auto search algorithm uses criteria based on the location of fat, calcium and contour inflection points to automatically determine locations of the four major coronary arteries (RM, LAD, CIRC, and RCA). The software determines the locations with 3-D coordinates which are displayed onto a 3-D surface rendered image of the heart. Each artery location is highlighted and identified. The operator may override the software and input corrections on the locations of the arteries. Once the arteries are located, a 3-D search ROI is automatically placed around the line locating the arteries without operator input. The software then searches each region within the 3-D ROIs encompassing each vessel to identify plaque above a calibrated threshold value. Since the CT images are calibrated with a calcium equivalent calibration phantom and further corrected with an in vivo blood sample measure, the threshold values are reproducible and independent of scanner type and patient size and body composition.

The locations of calcified plaque above the calibrated threshold are recorded along with their x,y,z coordinates. Positive calcifications are also automatically identified with the artery in which they are located. On repeat scans at a later date, comparison of calcium increase or decrease can be carried out because of the calibration methods and known calcification locations.

The methods improve reproducibility by use of the calibration methods and automatic location and quantification. Reproducibility is also improved due to the use of machine defined objective and reproducible criteria. The automatic algorithm greatly speeds the exam as each individual CT slice and each individual calcification need not be identified and analyzed.

Two additional methods to analyze coronary calcium are disclosed which do not require specific locations of the coronary arteries. In both methods, the boundaries of the heart are located and segmented from surrounding tissue. The heart volume with coronary arteries is analyzed as a 3-D volume with measured volume, shape and mass. A coordinate system is determined for the heart using the location of the center of the aorta as the superior coordinate. In one method the heart is divided into three regions from the inferior end to the superior end of the heart. The lower, inferior region, is known to have calcium only in the coronary arteries. The mid one third of the heart will usually contain the valves, which are sometimes calcified. It is desirable to exclude this calcium from the coronary calcium measure. A high calcium content in the region is a flag for the operator to evaluate and potentially remove the contribution from calcified valves. A search ROI can be placed around such regions and the calcium content subtracted from the total calcium measure. Alternatively, the calcium is located with x,y,z coordinates referenced to the heart volume coordinates. An algorithm defines the heart region for analysis as a shell surrounding the heart wall in 3-D space. Only calcium with a specified distance from the heart boundaries is included. The superior one-third of the heart is analyzed next. The aorta will be located in this region, and frequently contains calcium. It is desirable to exclude this calcium from the measure. The operator can evaluate high calcium content for this region and remove aortic calcium by manual ROI placement and subtraction. This method may provide high reproducibility and does not require specific coronary artery locations to be determined. The locations of calcium are, however, not identified with specific arteries.

A modification of this method does not divide the segmented heart volume into three regions, but rather analyzes only the surface shell region of the heart. The coronary arteries are known to be located exterior to the heart muscle wall and in between heart wall tissue. The coronary arteries can therefore be assumed to be located near the heart boundaries and outside the heart muscle. From the segmented heart volume, the surface coordinates of the heart are defined. The search ROI is set on the surface shell with a defined thickness of several pixels. Calcifications exceeding the set threshold are quantified. Valve calcium and aortic calcium are excluded based on their locations. In some cases, the aortic calcium will be included and will require manual exclusion.

In a second preferred embodiment of the invention, calcium in the aorta is quantified automatically and reproducibly. In this method, the calibration phantom is preferably first located automatically by prior art methods. The vertebral bodies are next located automatically, also by prior art methods. The exterior cortical margins of the vertebral bodies are located automatically by segmentation methods. A search ROI is placed automatically anterior to the cortical margin, which, with high probability, will encompass the aorta. The images within the search ROIs are cropped and reformatted to sagittal and coronal views. The reduced quantity of overlying tissue provides 2-D images with heightened contrast which can display the aorta and calcifications. The operator provides the superior and inferior limits of the aorta on the sagittal view or coronal view. A connecting line between these two points should intersect the aorta on all slices. If not, a third cursor click or more may be required. The intersection of the line and the aorta region provides a seed point for the software. Region growing methods or other similar methods are used to locate the aorta boundaries automatically. The boundaries are then searched with calibrated threshold criteria to identify calcifications in the aorta. The software determines the location of calcium in 3-D space. The results are displayed on the sagittal view, with exaggerated contrast if required to clearly show their presence and location. The calcium is summed and presented as a calcium measure which may or may not be normalized to the cross sectional area of the aorta or to the aorta volume.

In a second preferred method to automatically quantify calcium in the aorta, a different auto search algorithm is used. This algorithm has advantages in older patients who may have rotated vertebral bodies.

Either search algorithm will operate on any major artery of the body, including the carotids. Either algorithm can operate with or without calibration. However, performance is improved with external calibration using a phantom and internal calibration using blood as a surrogate internal calibration sample.

In accordance with certain embodiments described herein, a method measures calcium in arteries of the human body using computed tomography (CT). The method acquires CT images containing voxels representative of x-ray attenuation in the body. The method comprises calibrating the CT images. The method further comprises identifying the location of at least one artery automatically. The method further comprises identifying calcium within the artery automatically. The method further comprises quantifying the calcium using the calibrated CT image.

In accordance with certain other embodiments described herein, an automated method measures coronary calcium in a living subject using x-ray computed tomography (CT). The method acquires at least one CT image containing voxels representing x-ray attenuation of the subject. The method of analysis requires operator interactions and comprises analyzing the images in a computer to identify the boundaries of the heart. The method further comprises identifying the approximate location of at least one coronary artery. The method further comprises placing a region-of-interest (ROI) surrounding the artery location. The method further comprises analyzing the ROI to identify voxels above a threshold value. The method further comprises determining the calcium content.

In accordance with still other embodiments described herein, a method measures coronary calcium in a living subject using x-ray computed tomography (CT). The method acquires at least one CT image containing voxels representing x-ray attenuation of the subject. The method of analysis of the images comprises identifying the approximate location of at least one coronary artery. The method further comprises placing a region-of-interest (ROI) surrounding the artery location. The method further comprises analyzing the ROI to identify voxels above a threshold value. The method further comprises determining the calcium content.

In accordance with still other embodiments described herein, a system quantifies calcium in coronary arteries of the body using x-ray computed tomography (CT). The system comprises means for acquiring images of the arteries. The images are calibrated with a calcium equivalent phantom. The system further comprises means for determining the approximate location of at least one coronary artery automatically. The system further comprises means for automatically positioning a search ROI which surrounds the artery location on at least one image. The system further comprises means for evaluating image elements within said ROI to locate calcium. The system further comprises means for quantifying the calcium in the artery to generate a total calcium measure.

In accordance with still other embodiments described herein, a method determines calcium in arteries in a living body from at least one computed tomography image. The image comprises image elements representative of x-ray attenuation in said body. The method comprises scanning a calcium equivalent calibration referenced phantom simultaneously with the body. The method further comprises multiplying said image elements by the phantom calibration equation. The method further comprises automatically locating the calcium in the artery. The method further comprises determining the mass of calcium.

In accordance with still other embodiments described herein, a system determines calcium in at least one artery of a living subject using at least one x-ray computed tomography image. The system comprises means for locating a position of the artery on at least one image without operator interaction. The system further comprises means for placing regions-of-interest (ROI) surrounding the position of artery without operator interaction. The system further comprises means for locating calcium within the ROI without operator interaction. The system further comprises means for quantifying the calcium.

In accordance with still other embodiments described herein, a method quantifies calcium in at least one artery of a human subject from at least one computed tomography image. The method comprises scanning a reference calibration phantom containing calcium simultaneously with the subject. The method further comprises calibrating at least one image element using the calibration phantom. The method further comprises locating image elements within an image region corresponding to blood or the heart. The method further comprises determining a best measure of the density values of image elements within the image region. The method further comprises determining a calibration equation using the slope of HU values from the calibration phantom and intercept from said best measure. The method further comprises correcting image elements within the image by the calibration equation. The method further comprises identifying image elements above a threshold value. The method further comprises determining calcium within the artery.

In accordance with still other embodiments described herein, a method quantifies calcium in the aorta of a living subject from at least one computed tomography image. The method comprises locating a vertebral body in at least one image. The method further comprises locating an exterior cortical bone margin of the vertebral body in the image. The method further comprises defining a plurality of search contours. The method further comprises identifying calcified regions along each search contour having density values above a predetermined threshold value. The method further comprises quantify calcium in the aorta.

In accordance with still other embodiments described herein, a method measures calcification in the aorta of a living subject. The method comprises automatically defining a search region-of-interest (ROI) anterior to a vertebral body. The search ROI encompasses the aorta. The method further comprises locating boundaries of the aorta. The method further comprises identifying calcified regions within the boundaries of the aorta having densities above a predetermined threshold value. The method further comprises measuring a calcium content.

In accordance with still other embodiments described herein, a method automatically identifies approximate locations of coronary arteries of a living body within a plurality of images of a heart region of the body. Each image comprises image elements indicative of densities of corresponding body structures, and each image element has corresponding position coordinates. The method comprises (a) identifying a two-dimensional surface boundary of the heart in each image. The surface boundary is represented as a surface contour in the image. The method further comprises (b) searching the surface contour of an image for inflection point image elements and recording the position coordinates for each inflection point image element. The method further comprises (c) searching the surface contour of the image for groups of fat density image elements and recording the position coordinates for each fat density image element. Each group of fat density image elements comprises a group of neighboring image elements defining a volume greater than or equal to a predetermined fat threshold volume. Each fat density image element has a density value within a predetermined value range. The method further comprises (d) searching the surface contour of the image for groups of calcium density image elements and recording the position coordinates for each calcium density image element. Each group of calcium density image elements comprises a group of neighboring image elements defining a volume greater than or equal to a predetermined calcium threshold volume. Each calcium density image element has a density value greater than or equal to a predetermined threshold value. The method further comprises repeating (b)-(d) for subsequent images until all the two-dimensional surface boundaries are completely searched. The method further comprises (f) assigning a first weighting factor to each inflection point image element, a second weighting factor to each fat density image element, and a third weighting factor to each calcium density image element. The method further comprises (g) calculating a set of lines. Each line provides an approximate location of a coronary artery and corresponds to a weighted location average of the inflection point image elements, the fat density image elements, and the calcium density image elements.

In accordance with still other embodiments described herein, a method measures coronary artery calcification of a living body. The method comprises providing a plurality of noninvasive internal images of the body. Each image comprises image elements indicative of densities of corresponding body structures. The method further comprises identifying boundaries of the heart within the plurality of images, the boundaries defining a heart volume. The method further comprises dividing the heart volume into an inferior region, a middle region, and a superior region. The method further comprises locating calcium within the inferior region and attributing the inferior region calcium to calcification of the coronary arteries. The method further comprises locating calcium within the middle region and attributing a portion of the middle region calcium to calcification of the coronary arteries and a remaining portion of the middle region calcium to calcification of the heart valves. The method further comprises locating calcium within the superior region and attributing a portion of the superior region calcium to calcification of the coronary arteries and a remaining portion of the superior region calcium to calcification of the aorta.

In accordance with still other embodiments described herein, a method measures coronary artery calcification of a living body. The method comprises providing a plurality of noninvasive internal images. Each image comprises image elements indicative of densities of corresponding body structures. The method further comprises identifying boundaries of the heart within the plurality of images, the boundaries defining a heart volume. The method further comprises defining surface coordinates of the heart volume. The method further comprises defining a shell volume at the surface coordinates. The shell volume has a predetermined thickness. The method further comprises identifying calcified regions within the shell volume having density values above a predetermined threshold value and attributing the calcified regions to calcification of the coronary arteries.

DETAILED DESCRIPTION OF PREFERRED EMBODIMENTS

Figure 1:
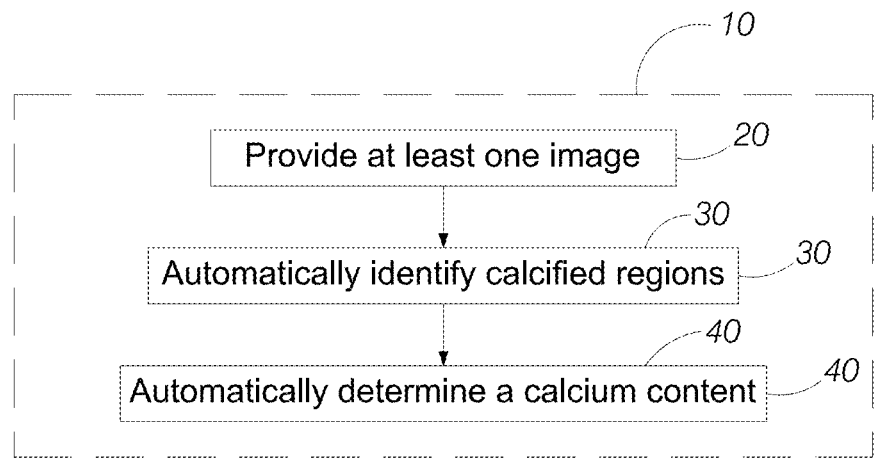
FIG. 1 is a flow diagram of an exemplary embodiment of a method for measuring calcification in at least a portion of the vascular system of a living body.

A premise of certain embodiments described herein is that the atherosclerotic process is systemic, affecting all of the arteries of the body in a similar way. Although plaque build-up may occur and/or progress at different rates in different arteries, this process occurs throughout the body. Others have studied the close relationship of cardiac calcium and extra-coronary plaque by comparing ultrasound measurements of carotid, aortic, and femoral plaque with ultrafast CT measurements of coronary calcifications. These studies have shown that patients with coronary calcifications had a higher prevalence of aortic and femoral plaque.

The abdominal aorta is a site of atherosclerotic plaque containing calcifications. The aorta has minimal motion, thus allowing easy imaging using conventional CT scanners. Although aortic calcifications have been associated subjectively with atherosclerotic disease, aortic calcium has not been quantified or proposed as a quantitative diagnostic test for generalized cardiovascular risk. Measurements of coronary and aortic calcium in 200 patients using a fast CT scanner with phantom calibration have shown a strong correlation between aortic and cardiac calcifications.

Although CT images are inherently quantitative, the recorded attenuation values, expressed in Hounsfield units ("HU"), can vary significantly due to a variety of technical factors. These factors include, but are not limited to, patient size and composition, and scanner-dependent factors such as beam hardening and scattered x-ray photons. The effective x-ray beam energy and the beam hardening error can vary with scanner design, x-ray tube and filtration, software functions and corrections, geometry, and body composition. Significantly different attenuation values for the same subject may be recorded on different CT machines. Even when the same CT machine is used, the attenuation values may vary at different times due to x-ray tube aging and/or electronic drift.

Calibration phantoms can provide a method to precisely quantify the attenuation by overcoming technical variations in CT scanners and physical differences from patient to patient. For example, QCT bone densitometry measurements of the lumbar spine have been improved by scanning phantoms simultaneously with the patient to calibrate the image to a known standard. Exemplary calibration processes are described by Arnold in U.S. Pat. No. 4,922,915, and in U.S. patent application Ser. No. 09/989,995, both of which are incorporated in their entirety by reference herein.

Quantitative CT measurements are typically facilitated by manual placement of a region-of-interest ("ROI") within specific areas of the CT image to be measured in HU units. The ROI is usually shown on a video screen as a bright line outline which has known (x,y) coordinates in the image voxel matrix. The ROI is adjustable for size, shape, or size and shape, and is positioned by the operator in the target area of individual CT slices by manually moving the ROI under cursor control using a keyboard, a light pen, or a mouse. Such manual procedures are laborious and time consuming, as well as being prone to error in exact positioning. In addition, many objects in the image, such as calcified plaque, have an irregular margin such that a fixed geometry ROI will typically be overinclusive by containing some non-calcified surrounding tissue or will be underinclusive by omitting a portion of the calcified plaque. Such errors can be quite large depending on the detail size.

Prior art software systems for coronary calcium measurements utilize a search ROI manually placed by the operator to aid the software in locating the target region. Typically, the search ROI is much larger than the target detail and is manually placed to fully surround the target region. The software then uses thresholding to aid in identifying the calcifications. For example, voxels anywhere in the image with HU values greater than a predetermined value are colored or highlighted. The operator then places the search ROI around the highlighted calcifications by using a mouse, a cursor, or a pointer to manually move the search ROI. Even though this manual procedure significantly aids the software in locating and analyzing the calcifications, the operator is required to manually place the search ROI or pointer on all CT images and on all calcified regions within each image. Such exemplary prior art software systems are described by Arnold in U.S. Pat. No. 4,922,915; Judd E. Reed et al. in *System for Quantitative Analysis of Coronary Calcification via Electron Beam Computed Tomography, SPIE Proceedings*, Vol. 2168, Medical Imaging 1994, *Physiology and Function from Multidimensional Images*, Eric A. Hoffman and Raj S. Acharya, eds., pp. 43-53; A. S. Agatston et al. in *Quantification of Coronary Artery Calcium Using Ultrafast Computed Tomography, J. Am. Coll. Cardiol.*, Vol. 15, 1990, pp. 827-832; R. Detrano et al., in *Accurate Coronary Calcium Phosphate Mass Measurements from Electron Beam Computed Tomograms, Am. J. Card. Imaging*, Vol. 9, No. 3, July 1995, pp. 167-173; and ScImage, Inc. of Los Altos, Calif., in *Calcified Plaque Analysis (CPA)*, commercial brochure, 2001, all of which are incorporated in their entireties by reference herein.

However, manually placing the search ROI limits the usefulness of CT imaging for calcium measurements. To cover the whole heart for coronary calcium measurements, several CT image slices are required. The operator must display and analyze each CT image slice and manually place one or more search ROIs in each image corresponding to the calcified regions in the image. The operator must use judgment in placing the search ROIs, which can lead to errors and loss of reproducibility on follow-up scans, thus degrading the ability to monitor changes in calcification. Similarly, manual placement of the search ROIs for aortic calcium measurements, requiring on the order of forty or more CT image slices, would be very laborious and impractical in a busy CT clinic. For quantification of coronary, aortic, or vascular calcifications anywhere in the body, many CT image slices are required, and manual analysis is very time consuming and subject to human error. It is therefore desirable to have automatic software methods for analysis of calcification using CT images which are fast and reliable.

Certain embodiments described herein provide an automatic and accurate method of quantifying coronary or aortic calcification using conventional single-slice CT scanners or MSCT scanners. Use of embodiments described herein can provide a safe, easy, noninvasive test for cardiovascular disease, which can be readily performed in most communities by using lower-cost conventional CT scanners. Certain such embodiments identify and locate the coronary arteries and/or aorta automatically, rather than by operator input.

In describing various embodiments, the terminology used herein is not intended to be interpreted in any limited or restrictive manner, simply because it is being utilized in conjunction with a detailed description of certain exemplary embodiments. Furthermore, embodiments may include several novel features, no single one of which is essential to practicing embodiments described herein.

Many embodiments described herein are useful in computer-implemented analysis processes of CT images. In these processes, CT imaging data are analyzed using software code running on general purpose computers, which can take a wide variety of forms, including, but not limited to, network servers, workstations, personal computers, mainframe computers, and the like. The code which configures the computer to perform these analyses is typically provided to the user on a computer-readable medium, such as a CD-ROM. The code may also be downloaded by a user from a network server which is part of a local or wide-area network, such as the Internet.

The general purpose computer running the software will typically include one or more input devices such as a mouse and/or keyboard, a display, and computer-readable memory media such as random access memory integrated circuits and a hard disk drive. One or more portions of the code or all of the code may be remote from the user and, for example, resident on a network resource such as a LAN server, Internet server, network storage device, etc. In typical embodiments, the software receives as an input a variety of information, such as the CT imaging data and any user-determined parameters for the analysis.

Embodiments are described herein using flow diagrams that have steps in a particular order, and the order of the steps in the flow diagrams is not to be considered to be limiting. Other methods with different orders of steps are also compatible with embodiments described herein. In addition, other methods with additional steps are also compatible with embodiments described herein.

FIG. 1 is a flow diagram of an exemplary embodiment of a method 10 for measuring calcification in at least a portion of the vascular system of a living body. The method 10 comprising providing at least one x-ray computed tomography (CT) image comprising voxels indicative of x-ray attenuation of corresponding body structures in an operational block 20. The method 10 further comprises automatically identifying calcified regions within the CT image in an operational block 30. The calcified regions have x-ray attenuation values above a predetermined threshold value. The method 10 further comprises automatically determining a calcium content corresponding to the identified calcified regions in an operational block 40.

Figure 2:
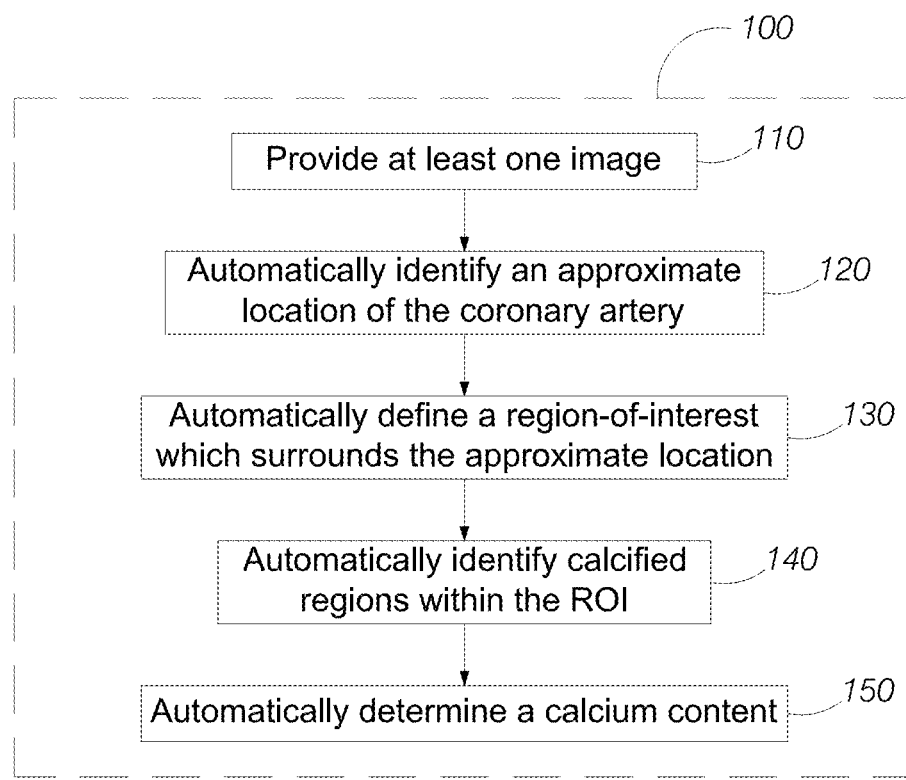
FIG. 2 is a flow diagram of an exemplary embodiment of a method for measuring calcification in at least one coronary artery of a living body.

FIG. 2 is a flow diagram of an exemplary embodiment of a method 100 for measuring calcification in at least one coronary artery of a living body. The embodiment of the method 100 illustrated by FIG. 2 comprises providing at least one CT image comprising voxels indicative of x-ray attenuation of corresponding body structures in an operational block 110. The method 100 further comprises automatically identifying an approximate location of the coronary artery within the CT image in an operational block 120. The method 100 further comprises automatically defining a region-of-interest (ROI) which surrounds the approximate location of the coronary artery in an operational block 130. The method 100 further comprises automatically identifying calcified regions within the ROI in an operational block 140. The calcified regions have x-ray attenuation values above a predetermined threshold value. The method 100 further comprises automatically determining a calcium content corresponding to the sum of the x-ray attenuation values of the identified calcified regions in an operational block 150.

In the operational block 110, at least one CT image is provided, the CT image comprises voxels indicative of x-ray attenuation of corresponding body structures. In certain such embodiments, a spiral or helical x-ray computed tomography (CT) scanner is used to generate a series of contiguous, two-dimensional axial CT images of cross-sectional views of the patient's internal organs. Each axial CT image comprises a plurality of voxels wherein the intensity of each voxel is representative of an x-ray attenuation value of a corresponding location within the body. Calcium has a higher density or x-ray attenuation value than does normal body tissue, so the axial CT images provide contrast between calcification and surrounding tissue. As used herein, voxels within the images which contain calcifications are referred to by the term "calcified regions."

Figure 3:
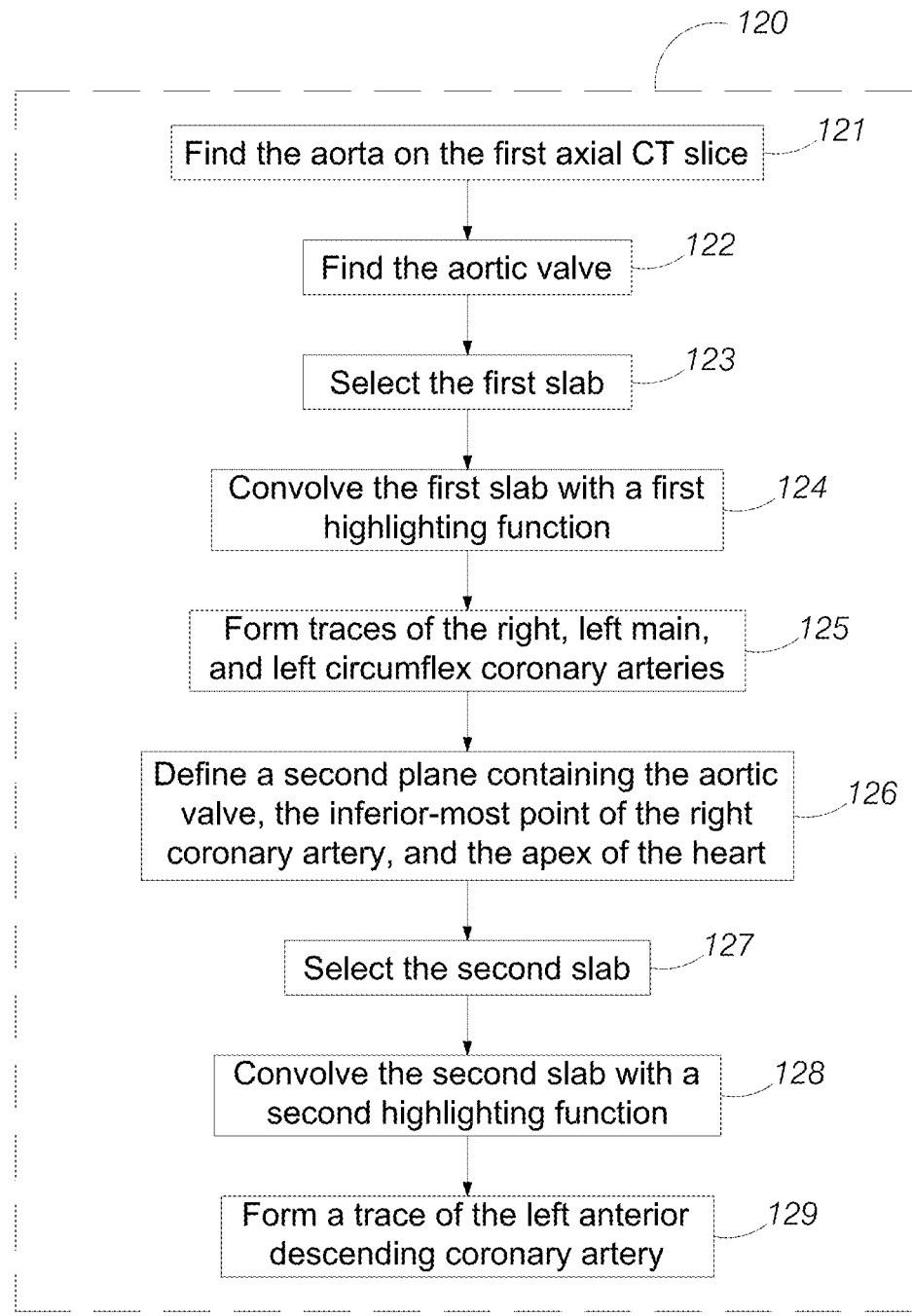
FIG. 3 is a flow diagram of one embodiment of a method for automatically identifying an approximate location of at least one coronary artery of a living body.

In the operational block 120, the approximate location of a coronary artery is automatically identified within the CT image. As used herein, the term "automatically identified" denotes that the operation of identifying details in the image by the computer system, in hardware, software, or both, rather than by the operator. FIG. 3 is a flow diagram of one embodiment of the operational block 120 in which each CT image is an axial CT slice of a three-dimensional x-ray CT image. The flow diagram of FIG. 3 refers to an embodiment in which the approximate locations of all four of the coronary arteries are automatically identified. Other procedures for approximately locating one or more coronary arteries are compatible with embodiments described herein, including procedures which permit operator intervention to correct for spurious results.

In the operational block 121, the aorta is found on a first axial CT slice (e.g., the axial CT slice which is at the top or the most superior position). In certain such embodiments, finding the aorta comprises identifying an aortic cross-section having a center in the first axial CT slice. The aortic cross section of certain embodiments is defined to be a sharp-edged, generally-circular object having a diameter between approximately 1.5 centimeters and approximately 3.0 centimeters, and having an x-ray attenuation value between approximately +20 HU and +40 HU. Furthermore, the aorta is typically bounded to the anterior and right side by the lungs, which have an x-ray attenuation value of approximately −800 HU.

In other embodiments, the aortic cross section is found on the first axial CT slice by cross-correlating the first axial CT slice with a model image. Because the ascending aorta is a cylindrical tube approximately parallel to the axis of the body, it appears as a circle in axial tomographic images. It is filled with blood with a density of slightly more than 1 g/ml and is surrounded by less dense fat and lung tissues. Thus, it is an easily identifiable object. The embodiment of a typical aorta identification method employs cross-correlation with a model image depicting a bright uniform 2-3 cm circle in a less dense background. This embodiment differs from standard cross correlation techniques by incorporating dynamic scaling to accommodate a range of aortic diameters.

In certain embodiments, the aortic cross-section of the first axial CT slice defines a coordinate system for the subsequent stages of the method 100. For example, the center of the aortic cross section can serve as a coordinate system origin. In addition, the locations of the coronary arteries can be determined to be a predetermined distance from this coordinate system origin. For example, the right coronary artery in certain embodiments is found to be one aortic diameter away from a plane that passes through the center of the aortic cross section at 45 degrees to the patient's spine.

In the operational block 122, the aortic valve is found by following the aorta down through subsequent lower axial CT slices in the inferior direction. In certain embodiments, finding the aortic valve comprises repeating the process of cross-correlation of the model image with subsequent axial CT slices in the inferior direction. Each axial CT slice will exhibit a corresponding cross section of the aorta as a circular body, as described above, shifted slightly from the position of the circular body in the previous axial CT slice. This process continues for subsequent axial CT slices in the inferior direction until an axial CT slice is found which does not exhibit a circular body corresponding to the aorta. This axial CT slice corresponds to the aortic valve at the interface between the aorta and the heart.

The heart has four large chambers: two atria and two ventricles. The ventricles and atria are separated by a planar structure. The aorta and pulmonary arteries are oriented such that they meet the ventricles at this plane as well. Thus, all four heart valves lie in approximately the same plane. The approximate location of this planar structure is readily identified on images from gross cardiac anatomy and by following the aorta to its terminus. As used herein, the term "valve plane" refers to this common plane. In the operational block 123, a first slab surrounding the valve plane is selected. The first slab can be selected by defining a generally planar region in the three-dimensional CT image which includes the aortic valve and is oriented at approximately 45 degrees from the axial direction. In certain embodiments, the thickness of the first slab is between approximately 1 centimeter and approximately 3 centimeters.

Certain embodiments exploit the fact that a large fraction of the course of coronary arteries along the surface of the heart coincides with the valve plane. The right coronary artery emerges from the right anterior side of the aorta just above the aortic valve and follows the valve plane right anterior margin of the valve plane. The left main coronary artery emerges from the left side of the aortic valve and quickly branches into the circumflex coronary artery which follows the posterior left margin of the valve plane.

The coronary arteries are positioned on the outer surface of the heart and each artery is generally surrounded by a region of fat tissue. In the operational block 124, the first slab is convolved with a first highlighting function to highlight a first set of voxels having blood x-ray attenuation values against a background of voxels having fat x-ray attenuation values. These "blood x-ray attenuation voxels" correspond to the coronary arteries. In certain embodiments, the first highlighting function has a bright spot surrounded by a dark ring. Various highlighting functions are compatible with embodiments described herein, including, but not limited to, the sinc function (i.e., $sinc(x)=sin(x)/x$). The Fourier transform of the sinc function is a rectangular function, thereby making the convolution of the sinc function with the first slab relatively easy to calculate. In the operational block 125, the first set of blood x-ray attenuation voxels are connected together to form traces of the right, left main, and left circumflex coronary arteries.

In the operational block 126, a second plane containing the aortic valve, the inferior-most point of the right coronary artery, and the apex of the heart is defined. The positions of the aortic valve and the inferior-most point of the right coronary artery are determined as described above. The position of the apex of the heart is determined by noting that the heart is positioned within a surrounding region of fat tissue and lung tissue. By searching generally perpendicularly to the valve plane (i.e., in the left anterior direction), the furthest-most transition from blood x-ray attenuation values to fat or lung x-ray attenuation values is found. This transition point is used as the apex of the heart to define the second plane.

In the operational block 127, a second generally planar slab surrounding this second plane is selected. In certain embodiments, the second slab has a thickness between approximately 1 centimeter and approximately 3 centimeters. In the operational block 128, the second slab is convolved with a second highlighting function to highlight a second set of blood x-ray attenuation voxels. In certain embodiments, the second highlighting function is the same as the first highlighting function, which in certain such embodiments is the sinc function. In the operational block 129, the second set of blood x-ray attenuation voxels are connected together to form a trace of the left anterior descending artery.

In the operational block 130, a region-of-interest (ROI) is automatically defined. The ROI surrounds the approximate location of the coronary artery. As used herein, the term "automatically defined" denotes that the operation of defining the ROI is performed primarily by the computer system in hardware, in software, or in both hardware and software, rather than by the operator. Various procedures for automatically defining the ROI are compatible with embodiments described herein, including procedures which permit operator intervention to correct for spurious results.

In certain embodiments, the ROI is defined to be a generally cylindrical volume surrounding the approximate location of the coronary artery. In certain such embodiments, the axis of the generally cylindrical ROI follows the trace of the coronary artery as determined herein. The radius of the generally cylindrical volume is large enough to encompass the entire coronary artery, and in certain embodiments, the radius is less than or equal to approximately one centimeter.

In the operational block 140, calcified regions are automatically identified within the ROI. The calcified regions have x-ray attenuation values above a predetermined threshold value. As used herein, the term "automatically identified" denotes that the operation of identifying the calcified regions is performed primarily by the computer system in hardware, in software, or in both hardware and software, rather than by the operator. Other procedures are compatible with embodiments described herein, including procedures which permit operator intervention to correct for spurious results. Exemplary procedures for automatically identifying calcified regions are described by A. S. Agatston et al., in *Coronary Calcification: Detection by Ultrafast Computed Tomography*, W. Stanford and J. A. Rumberger (eds.), *Ultrafast Computed Tomography: Principles and Practice*, Mount Kisco, N.Y., Futura Publishing Co., Inc., pp. 77-95, which is incorporated in its entirety by reference herein.

In certain embodiments, the calcified regions are automatically identified using a pair of criteria corresponding to (i) x-ray attenuation and (ii) size. Using the first criterion of x-ray attenuation, the voxels having x-ray attenuation values greater than or equal to a predetermined threshold value are identified. In certain embodiments using CT images, to qualify as a calcified region, the x-ray attenuation value of the voxel is greater than or equal to approximately 130 HU. In other embodiments, the predetermined threshold value is two standard deviations greater than the mean x-ray attenuation value of the CT image of the heart region. Other predetermined threshold values for the x-ray attenuation criterion are compatible with embodiments described herein.

Using the second criterion of size, the volume of the voxels neighboring one another and satisfying the x-ray attenuation criterion is calculated. In certain embodiments, a group of neighboring voxels having a total volume greater than or equal to a predetermined volume is interpreted as corresponding to calcified regions. For example, the predetermined volume of certain embodiments is two or more image elements, while in other embodiments, the predetermined volume is four image elements. This size criterion helps to avoid including random isolated noise in the calcium content determination. Other predetermined values for the size criterion are compatible with embodiments described herein.

Calibration phantoms can provide a method to precisely quantify the x-ray attenuation by overcoming technical variations in CT scanners and physical differences from patient to patient. For example, QCT bone densitometry measurements of the lumbar spine have been improved by scanning phantoms simultaneously with the patient to calibrate the image to a known standard. Exemplary calibration processes are described by Arnold in U.S. Pat. No. 4,922,915 and in U.S. patent application Ser. No. 09/989,995, both of which are incorporated in their entirety by reference herein.

In the operational block 150, a calcium content corresponding to the sum of the x-ray attenuation values of the identified calcified regions is automatically determined. As used herein, the term "automatically determined" denotes that the operation of determining the calcium content is performed primarily by the computer system in hardware, in software, or in both hardware and software, rather than by the operator. Other procedures are compatible with embodiments described herein, including, for example, procedures which permit operator intervention to correct for spurious results.

In certain embodiments, the x-ray attenuation values of all the calcified regions are calibrated and summed together to provide a measure of the calcium content expressed in mass units referred to the calibration phantom. This procedure can provide a good approximation of the total mass of the calcified regions. Other weighting procedures or summation procedures are compatible with embodiments described herein. In addition, as described herein, by calibrating the images, the voxel x-ray attenuation values can be converted to mass units.

In certain embodiments, the method 100 further comprises segmenting out portions from the three-dimensional CT image that do not correspond to the heart. Such a process identifies and omits from further analysis data regions that are not of interest. The process can simplify and/or speed up the subsequent analysis. While certain embodiments perform the segmentation prior to the operational block 120 of FIGS. 2 and 3, other embodiments perform the segmentation at other stages of the method 100.

Figure 4:
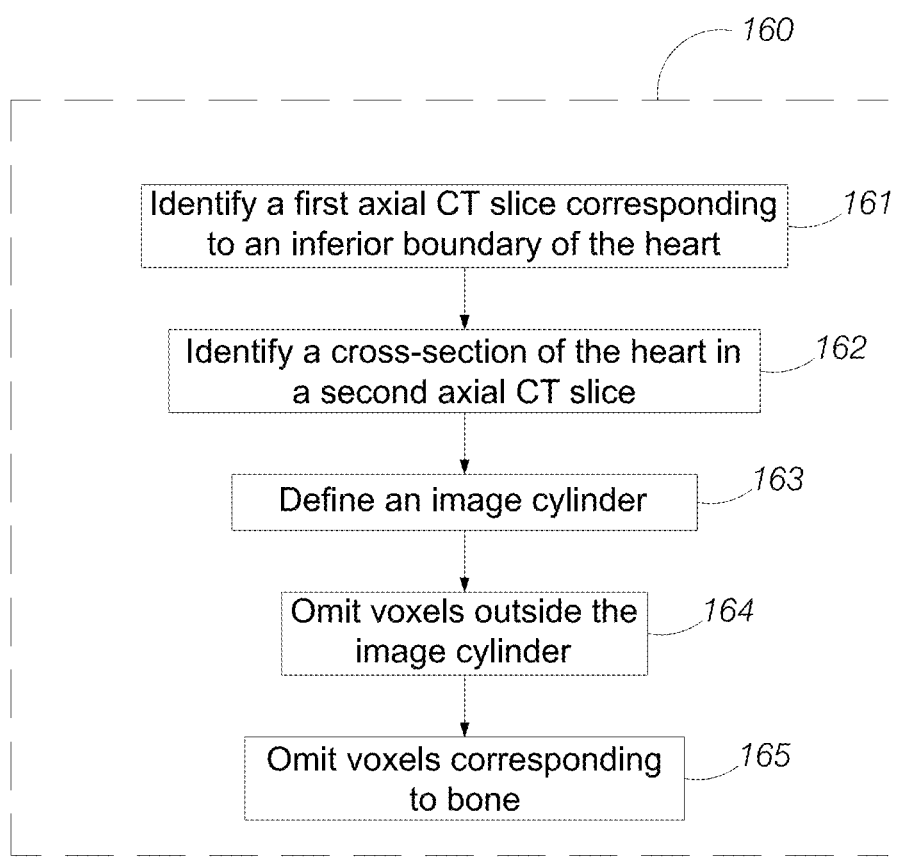
FIG. 4 is a flow diagram of one embodiment for segmenting out portions which do not correspond to the heart from an x-ray CT image.

FIG. 4 is a flow diagram of one embodiment of an operational block 160 for segmenting out portions from an x-ray CT image that do not correspond to the heart. The operational block 160, as illustrated by FIG. 4, provides a rough segmentation of the heart from the rest of the three-dimensional x-ray CT image. Other segmentation processes are compatible with embodiments described herein.

In certain embodiments, the operational block 160 comprises identifying a first axial CT slice corresponding to an inferior boundary of the heart in an operational block 161. In certain such embodiments, the first axial CT slice is identified automatically by the analysis system. A plot of the cross-sectional density as a function of the axial direction is produced by summing the x-ray attenuation values for the voxels in each axial CT slice. Because the x-ray attenuation values corresponding to lung tissue are lower than those corresponding to blood, fat, or muscle tissue, the largest change in the cross-sectional density between subsequent axial CT slices is deemed to denote the diaphragm (i.e., the boundary between the lungs and the liver). The diaphragm represents a uniformly present landmark which is positioned next to and in the inferior direction from the heart, so the first axial CT slice is typically the slice which denotes the diaphragm. In certain other embodiments, the first axial CT slice is identified by the operator, who provides operator input to the analysis system. Other procedures for identifying the first axial CT slice corresponding to the inferior boundary of the heart are compatible with embodiments described herein.

In certain embodiments, the operational block 160 further comprises identifying a cross section of the heart within a second axial CT slice in an operational block 162. The second axial CT slice is spaced a distance in the superior direction from the first axial CT slice. In certain embodiments, the distance is predetermined to be approximately one centimeter, and the cross section of the heart is identified to be the largest round object within the second axial CT slice. In other embodiments, each of the axial CT slices superior to the first axial CT slice is examined, and the largest round object within each of the axial CT slices is determined. The cross section of the heart is then identified to be the largest of these round objects from the axial CT slices. The cross section of the heart typically has a diameter of approximately 10 centimeters. Other procedures for identifying the cross section of the heart are compatible with embodiments described herein.

In certain embodiments, the operational block 160 further comprises defining an image cylinder in an operational block 163. The image cylinder has a cylinder diameter equal to a diameter of the heart cross section and has a cylinder axis at a predetermined orientation with respect to the axial direction. In certain embodiments, the cylinder axis of the image cylinder is selected to coincide with the axis of the heart so that the heart is within the volume defined by the image cylinder. The cylinder axis in certain embodiments is defined by starting at the center of the heart cross section in the second axial CT slice and in subsequent inferior slices, shifting the center anteriorly and to the left by a predetermined amount. Similarly, in subsequent superior slices from the second axial CT slice, the center is shifted posteriorly and to the right. The cylinder axis, defined to be the line defined by the center, is thus slanted to correspond to the axis of the heart. In certain other embodiments, the size, position, and orientation of the image cylinder can be determined in part by operator input. Other procedures for defining the image cylinder are compatible with embodiments described herein.

In certain embodiments, the operational block 160 further comprises omitting voxels from the image in an operational block 164. The omitted voxels are outside the volume defined by the image cylinder. In certain embodiments, omitting the voxels from the image comprises omitting the voxels from subsequent analysis steps, as opposed to removal of voxels from the image. In certain other embodiments, the image is modified to remove the omitted voxels.

In certain embodiments, the operational block 160 further comprises omitting voxels corresponding to bone within the volume defined by the image cylinder in the operational block 165. In certain such embodiments, the voxels corresponding to bone are identified to include voxels on the surface of the image cylinder having x-ray attenuation values above a threshold and voxels within the image cylinder connected to these surface voxels and having x-ray attenuation values above the threshold. In certain embodiments, the threshold is predetermined to be approximately 130 HU, while in other embodiments, the threshold is set to be larger than a mean x-ray attenuation value of the image cylinder volume. In certain embodiments, omitting the voxels corresponding to bone comprises omitting the voxels from subsequent analysis steps, as opposed to removal of voxels from the image. In certain other embodiments, the image is modified to remove the omitted voxels.

In certain embodiments, the method 100 further comprises calibrating the CT image. Such a process calibrates the image data using a calibration standard, enabling quantitative density measurements using the image data. While certain embodiments perform the calibration prior to the operational block 120 of FIGS. 2 and 3, other embodiments perform the calibration at other stages of the method 100.

In certain embodiments, measurements from a calcium-equivalent phantom are used to derive a calibration equation to calibrate the CT image. In other embodiments, measurements from an in vivo blood sample are used to derive the calibration equation. Such embodiments of calibrating the CT image are described, for example, in U.S. patent application Ser. No. 09/989,995, referenced above.

Figure 5:
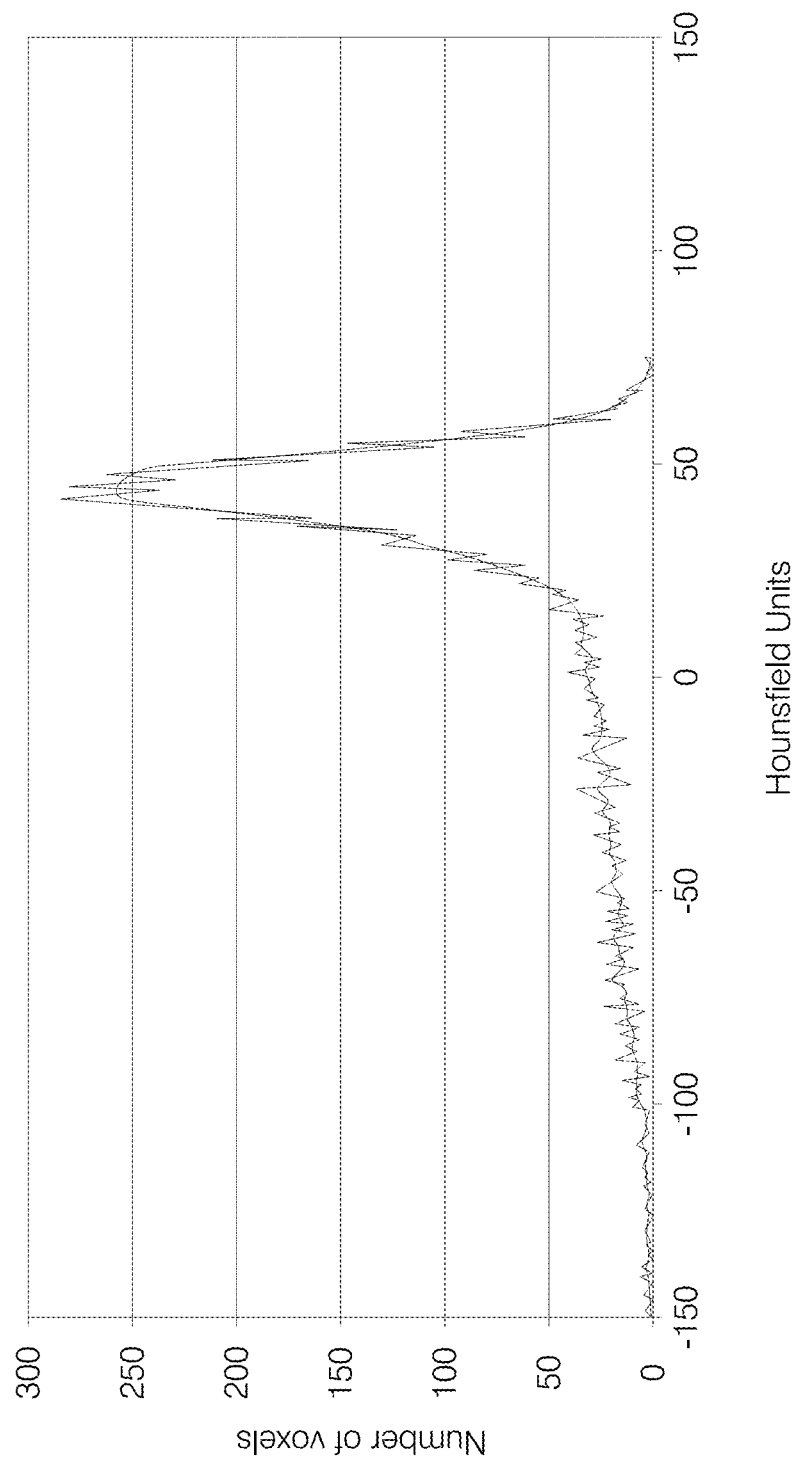
FIG. 5 illustrates an exemplary histogram of a CT image.

In certain embodiments, calibrating the CT image comprises generating a histogram of the x-ray attenuation values of the voxels of the CT image. Typically, such a histogram will exhibit one or more peaks corresponding to x-ray attenuation values for blood and muscle, fat, bones, and lungs. An exemplary histogram is illustrated in FIG. 5 for a CT image. One or more of these peaks can be then be used to calibrate the image. For example, a histogram of the x-ray attenuation distribution may exhibit a generally Gaussian peak due to blood and muscle tissue having a mean value between approximately +20 and +40 HU and a generally Gaussian peak due to fat tissue having a mean value between approximately −120 and −180 HU. A linear calibration equation can be calculated to shift the mean values of the two Gaussian peaks to +20 HU and −100 HU, respectively, and this calibration equation can be applied to the voxels of the CT image.

In certain embodiments, the method 100 further comprises removing streak artifacts from the CT image. While certain embodiments perform the removal of streak artifacts prior to the operational block 120 of FIGS. 2 and 3, other embodiments perform the removal at other stages of the method 100. In certain embodiments, removing streak artifacts comprises performing adaptive histogram equalization on the image, while other embodiments comprise performing non-adaptive histogram equalization on the image. Adaptive histogram equalization is performed by breaking the image into small, overlapping regions and applying histogram equalization to each region separately. The non-adaptive form of histogram equalization has been described by R. C. Gonzalez and P. Wintz in Digital Image Processing, 1977, Addison-Wesley Publishing Company, Reading, Mass., which is incorporated in its entirety by reference herein. Other image restoration procedures for removing streak artifacts or for otherwise smoothing out noise from the image are compatible with embodiments described herein.

Figure 6A:
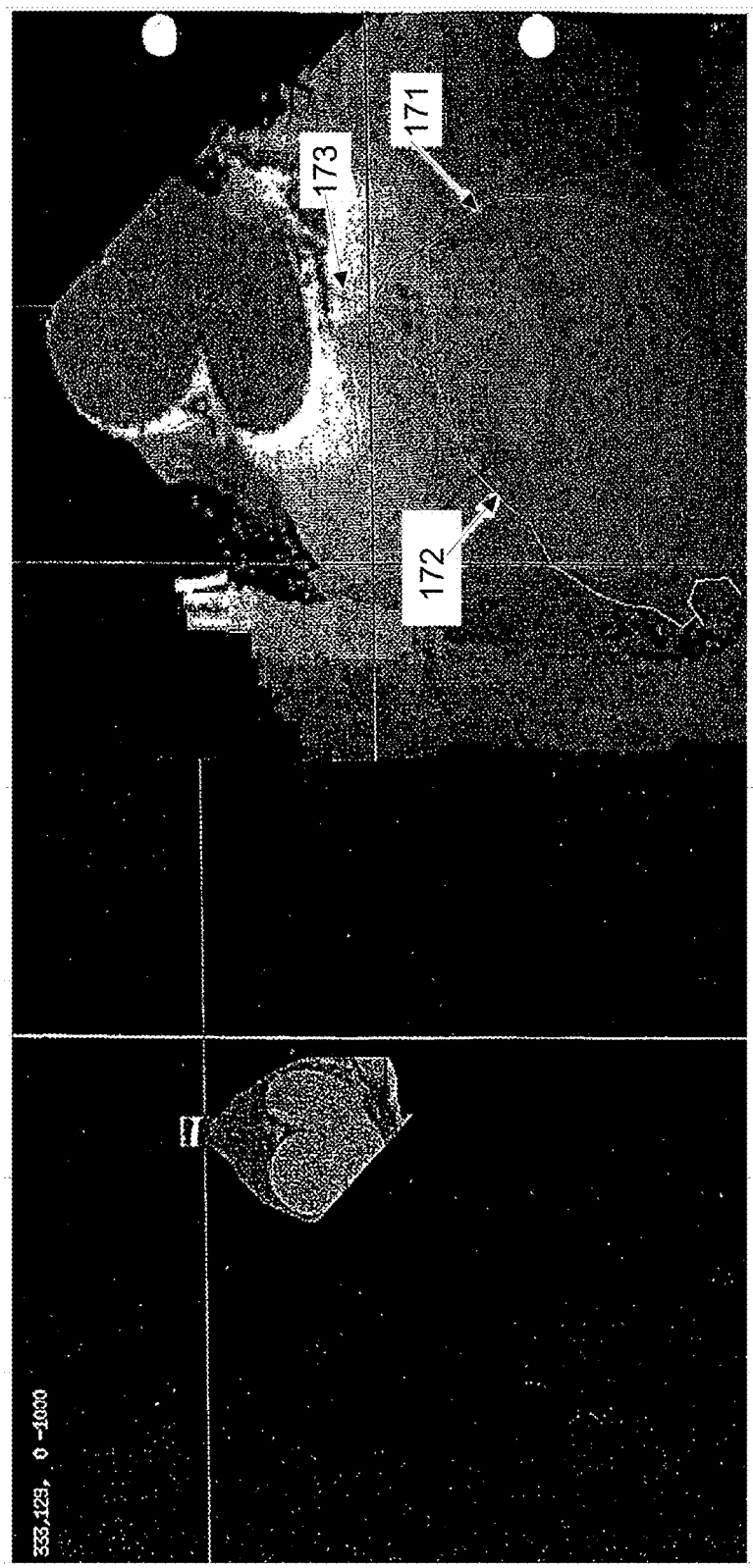
FIG. 6A schematically illustrates a surface rendered three-dimensional image of the heart showing the location of the right coronary artery, the left anterior descending artery, and the main coronary artery.
Figure 6B:
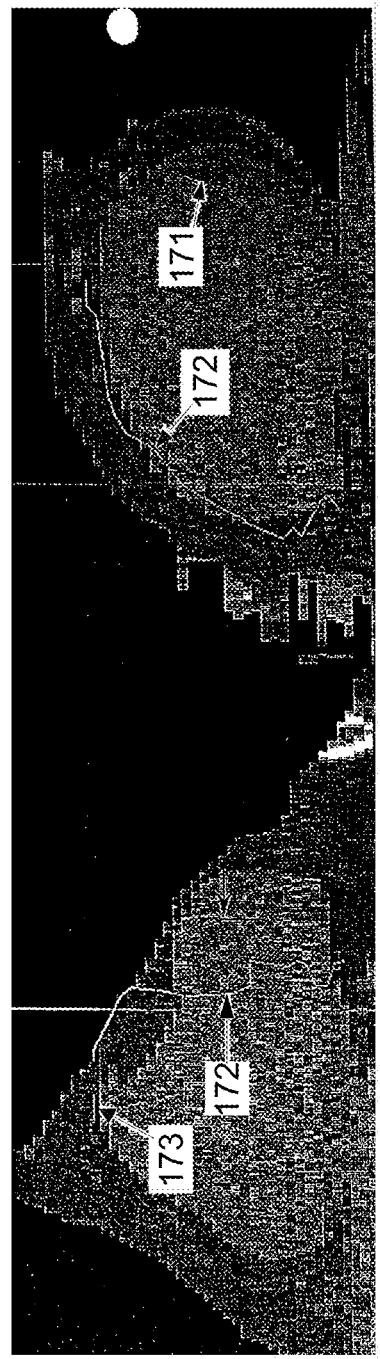
FIG. 6B schematically illustrates sagittal and coronal reformations of the data illustrated in FIG. 6A.

FIG. 6A schematically illustrates a surface rendered three-dimensional CT image of the heart showing the location of the right coronary artery 171, the left anterior descending artery 172, and the main coronary artery 173. These locations are determined in three-dimensional space with position coordinates representing the approximate locations of the coronary arteries. FIG. 6B schematically illustrates sagittal and coronal reformations of the data illustrated in FIG. 6A.

Figure 7A:
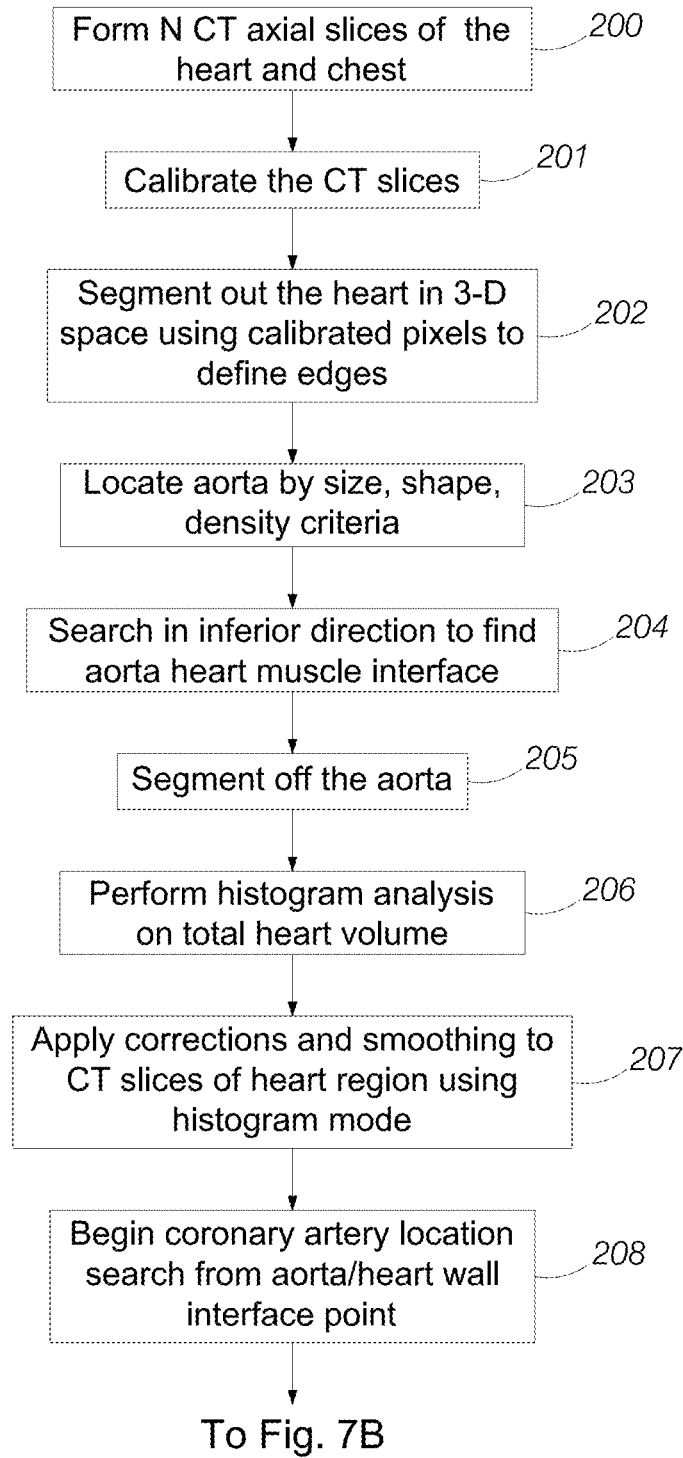
FIGS. 7A, 7B, and 7C illustrate a flow diagram of one embodiment of a method for measuring coronary artery calcification of a living body.
Figure 7B:
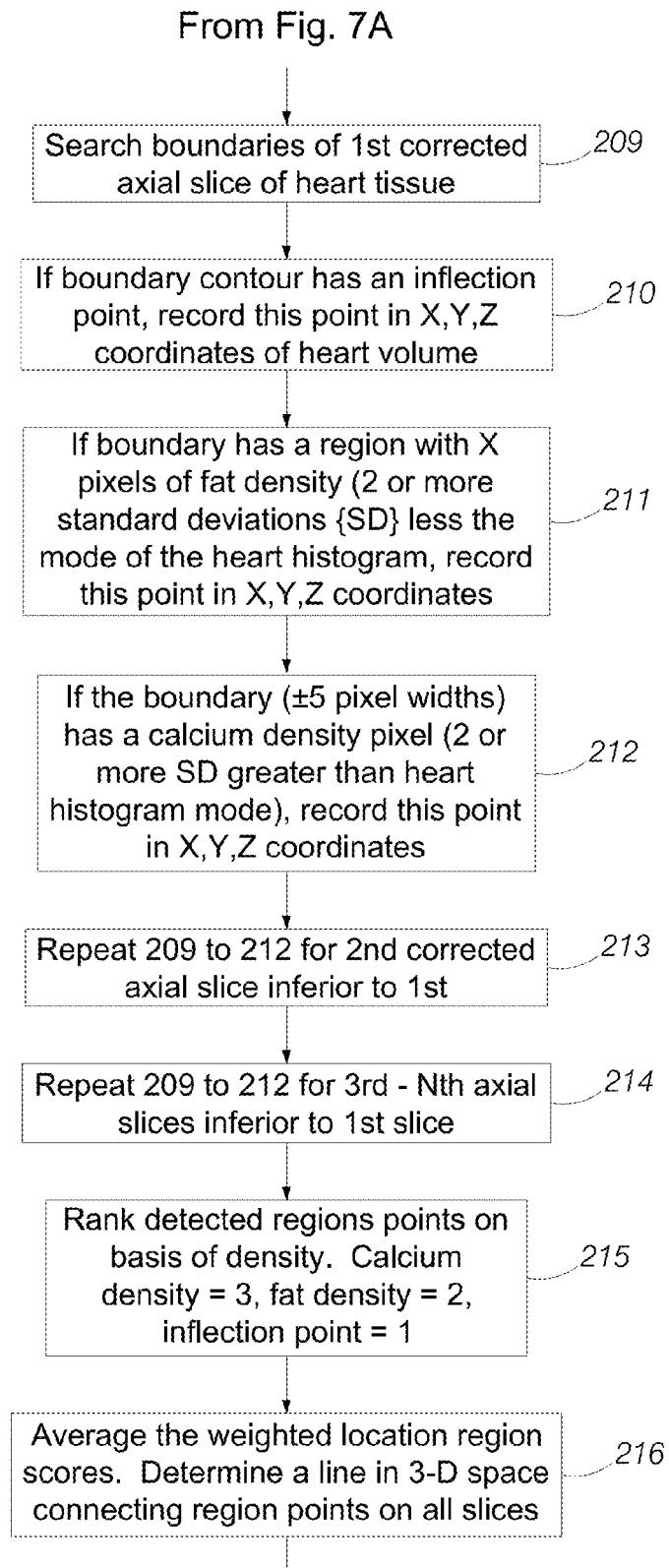
Figure 7C:
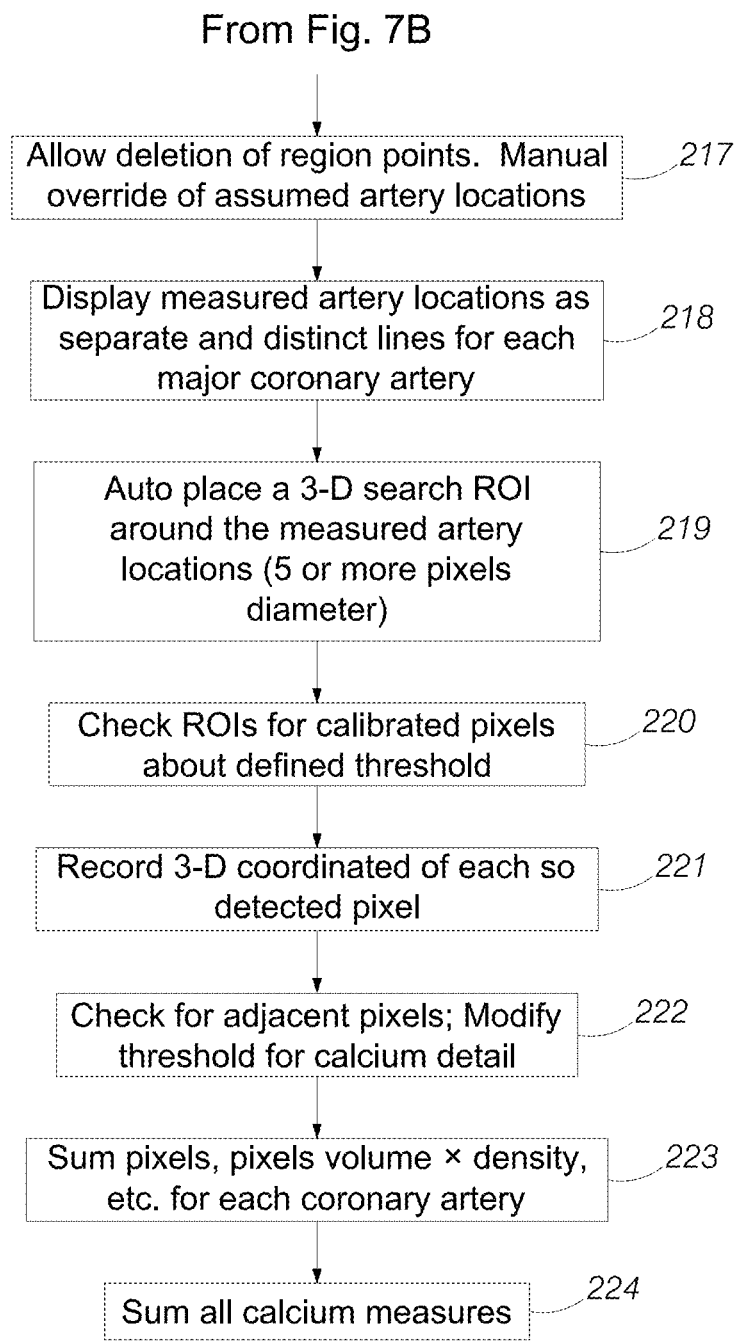

FIG. 7, comprising into FIGS. 7A, 7B, and 7C, is a flow diagram of another embodiment of a method for measuring coronary artery calcification of a living body. As shown in FIG. 7, N CT axial slices of the heart and chest are formed in a step 200, and calibration of the CT slices is performed in a step 201 using the calibration equation. The entire heart volume is segmented out in three-dimensional space using calibrated pixels to define edges in step 202. The aorta is located by size, shape, and density criteria in a step 203. The software automatically searches in the inferior direction to find the aorta and heart muscle interface in a step 204. Segmentation methods well known in the field are used to segment off the aorta in a step 205. A histogram analysis is next performed on the total heart volume in a step 206. It is useful to apply corrections and smoothing to CT slices of the heart region in a step 207. The smoothing routine creates a new image with mean pixel densities equal to the histogram mode of the entire heart.

The software begins coronary artery location search from the aorta/heart wall interface point in a step 208. The minimum aortic diameter and location of a most complete circular shape is used as a starting location. The first CT slice superior to the heart is displayed. The boundaries of the heart have previously been identified. Then, in a step 209, the boundaries of the first corrected axial slice are searched. If boundary contours have an inflection point, this point is recorded in x,y,z coordinates in a step 210. If the boundary has a region with one or more pixels of fat density, this region is recorded with x,y,z coordinates. If the boundary has a calcium density pixel (2 or more standard deviations greater than heart histogram mode), this region is recorded with x,y,z coordinates. The borders are preferably defined with a width of about 5 pixels.

In a step 213, the procedure of steps 209 to 212 is repeated for the second corrected axial slice inferior to the first slice. In a step 214, the procedure of steps 209 to 212 is repeated for all slices up to and including the Nth corrected axial slice inferior to the first slice. In a step 215, the detected regions are ranked for score based on calcium density being equal to 3, fat density being equal to 2, and inflection point being equal to 1. In a step 216, the weighted location scores are averaged to determine a line in three-dimensional space connecting points on all slices.

In a step 217, the operator may delete points as a manual override of assumed artery positions at any time. The artery locations in an x,y,z coordinate system are determined. The line identifying the locations is analyzed onto a three-dimensional surface rendered image in a step 218. As described above, FIG. 6A shows the surface rendered three-dimensional image of the heart with the location of the main coronary artery 173, the right coronary artery 171, and the left anterior descending artery 172. These locations are determined in three-dimensional space with x,y,z coordinates and represent the appropriate locations of the arteries. FIG. 6B shows sagittal and coronal reformations of the same data as FIG. 6A with the locations of three of the coronary arteries also shown on these views. The software automatically places a three-dimensional search ROI around the measured artery positions in step 219. The diameter of the three-dimensional ROI is small relative to the heart and is on the order of 5 or more pixels in diameter.

If, in a step 220, any pixels in the ROI are above the defined threshold, they are included. The location of the calcium is recorded with three-dimensional coordinates of each pixel in a step 221. Pixels which are adjacent on the slice or on adjacent slices will be considered in a step 222. The sum of voxels and the voxel volume times density for each coronary artery are summed on all images in a step 224, and the results are stored and printed as the final calcium measures. The calcium measure may be a calibrated calcium score or may be calcium mass.

Figure 8:
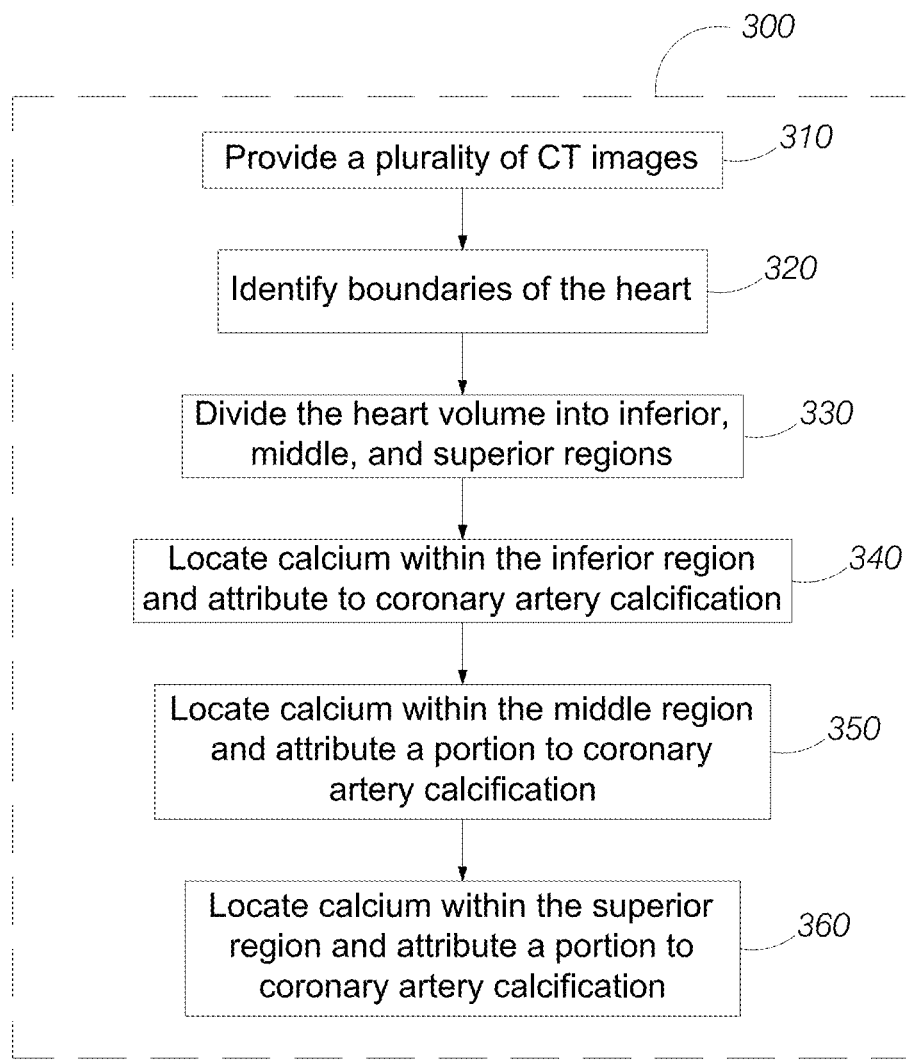
FIG. 8 is a flow diagram of another embodiment of a method for measuring coronary artery calcification of a living body.

FIG. 8 is a flow diagram of one embodiment of a method 300 for measuring coronary artery calcification of a living body. In an operational block 310, the method 300 comprises providing a plurality of CT images, and each CT image comprises voxels indicative of x-ray attenuation of corresponding body structures.

In an operational block 320, the method 300 further comprises identifying boundaries of the heart within the plurality of CT images, with the boundaries defining a heart volume. Several hundred HU separate blood and lung x-ray attenuations. Almost any threshold technique can be used to identify the boundaries of the heart within the images.

In an operational block 330, the method 300 further comprises dividing the heart volume into an inferior region, a middle region, and a superior region. From the end of the aorta, divide the heart into four quadrants. The right coronary artery is in a right anterior quadrant, the left anterior descending coronary artery is in a left anterior quadrant, the circumflex coronary artery is in a left posterior quadrant, and the fourth (right posterior) quadrant is empty of coronary arteries. Near the aorta (e.g., within 3 cm to the left of the aorta) is the left main coronary artery.

In an operational block 340, the method 300 further comprises locating calcium within the inferior region and attributing the inferior region calcium to calcification of the coronary arteries. Voxels corresponding to calcium can be identified as described above.

In an operational block 350, the method 300 further comprises locating calcium within the middle region, attributing a portion of the middle region calcium to calcification of the coronary arteries and attributing a remaining portion of the middle region calcium to calcification of the heart valves. In certain embodiments, the portion of the middle region calcium attributed to calcification of the coronary arteries comprises calcium within the middle region which is within a shell volume at an outer edge of the heart volume. In such embodiments, the shell volume has a predetermined thickness. The coronary arteries are typically within 2 cm of the surface of the heart.

In an operational block 360, the method 300 further comprises locating calcium within the superior region and attributing a portion of the superior region calcium to calcification of the coronary arteries and a remaining portion of the superior region calcium to calcification of the aorta. The aortic rim calcium is typically on the boundary of the aortic image which was followed as described above.

The methods described herein can be used to automatically locate other arteries in the body and to measure calcium. For example, a method to automatically locate and measure calcium in the abdominal aorta is shown in FIG. 9. Since the aorta does not move greatly, single slice and lower speed CT scanners can be used to acquire the images. From a complete exam of several CT slices, the method of this embodiment can be understood with reference to FIGS. 5, 9, 10, 11, and 14.

Figure 10:
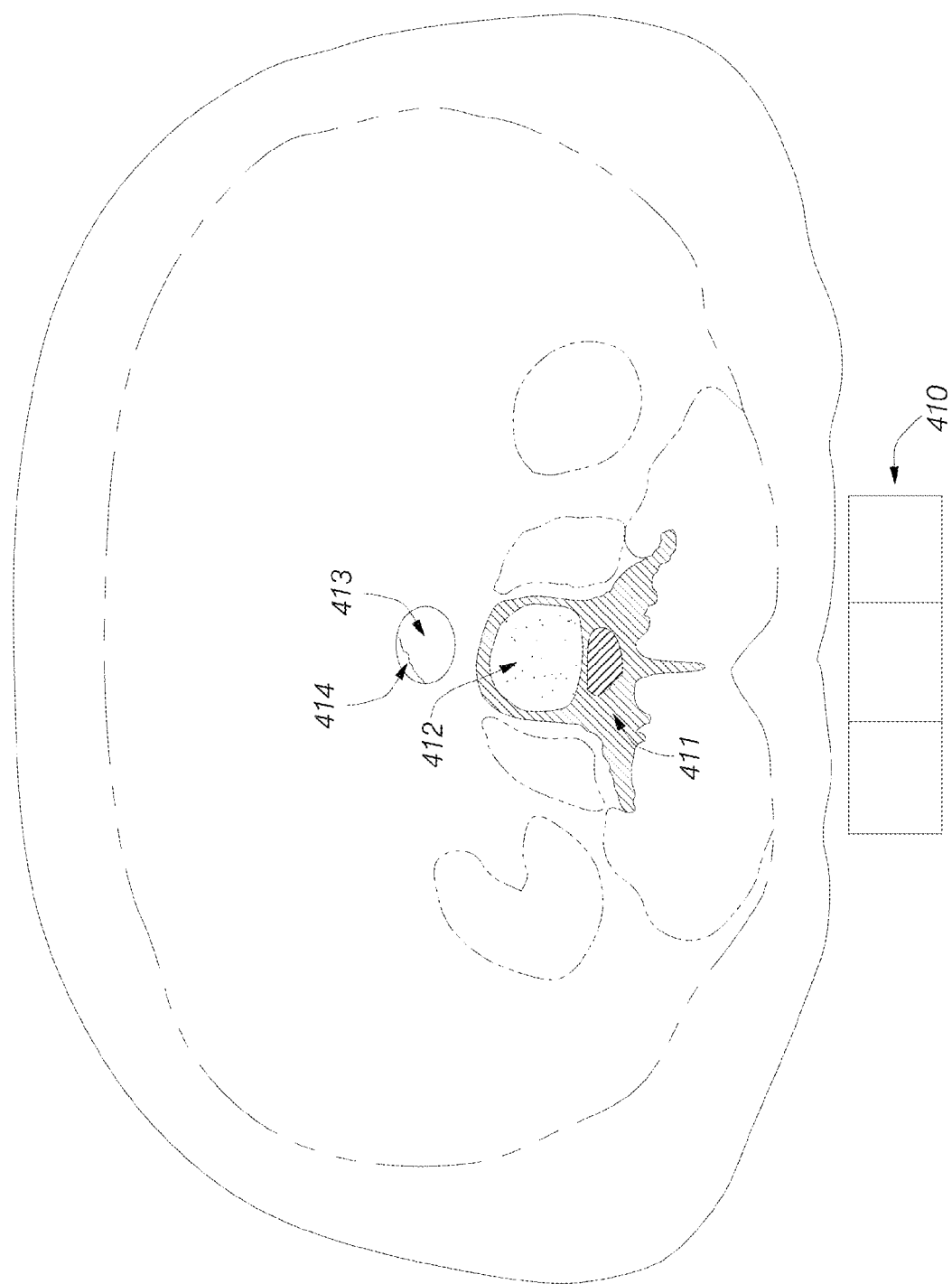
FIG. 10 illustrates a depiction of a cross section through the abdomen showing a calibration phantom, a vertebra, and the aorta with calcification.

FIG. 10 shows a depiction of a CT slice through the abdomen of a patient. The calibration reference phantom 410 contains three samples of varying calcium density. Other phantoms can be used in separate or simultaneous calibration. The trabecular region of one vertebral body 412 is surrounded by the dense cortical shell 411. The usual location of the abdominal aorta 413 is directly anterior to the vertebral body. Aortic calcification 414 is depicted.

Figure 9A:
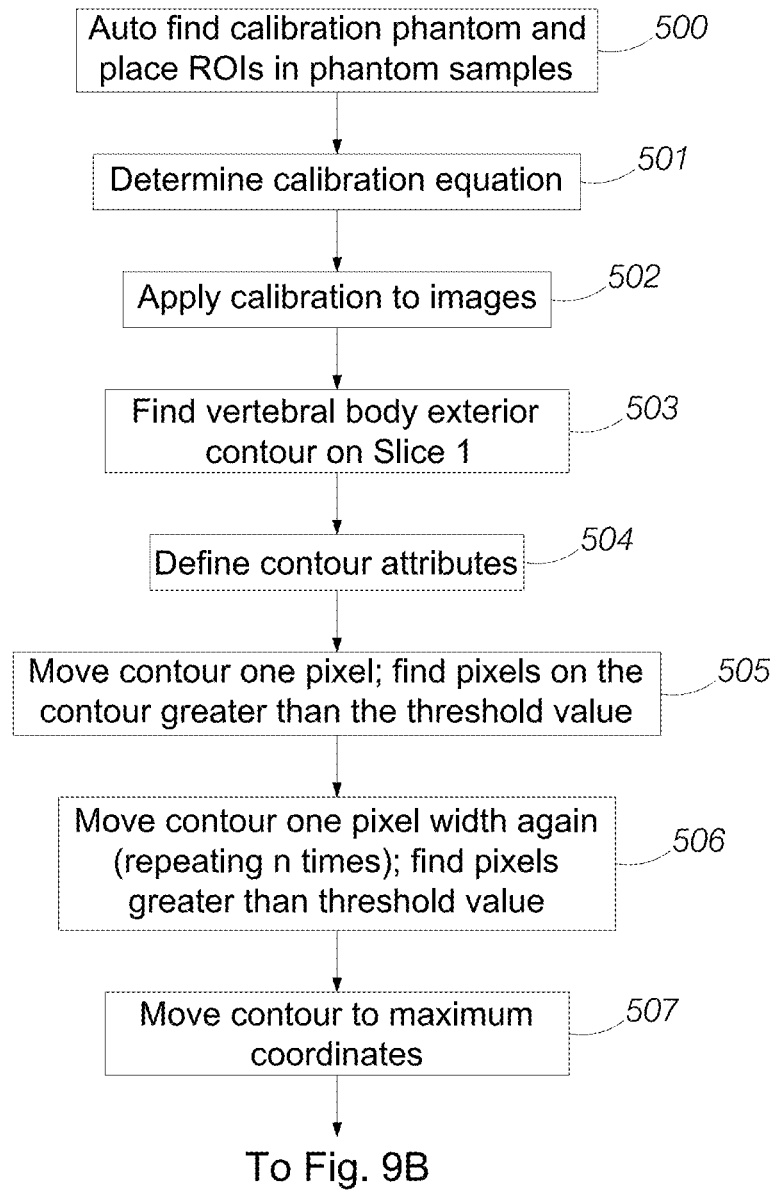
FIGS. 9A and 9B illustrate a flow diagram of another embodiment of a method of measuring coronary artery calcification of a living body.
Figure 9B:
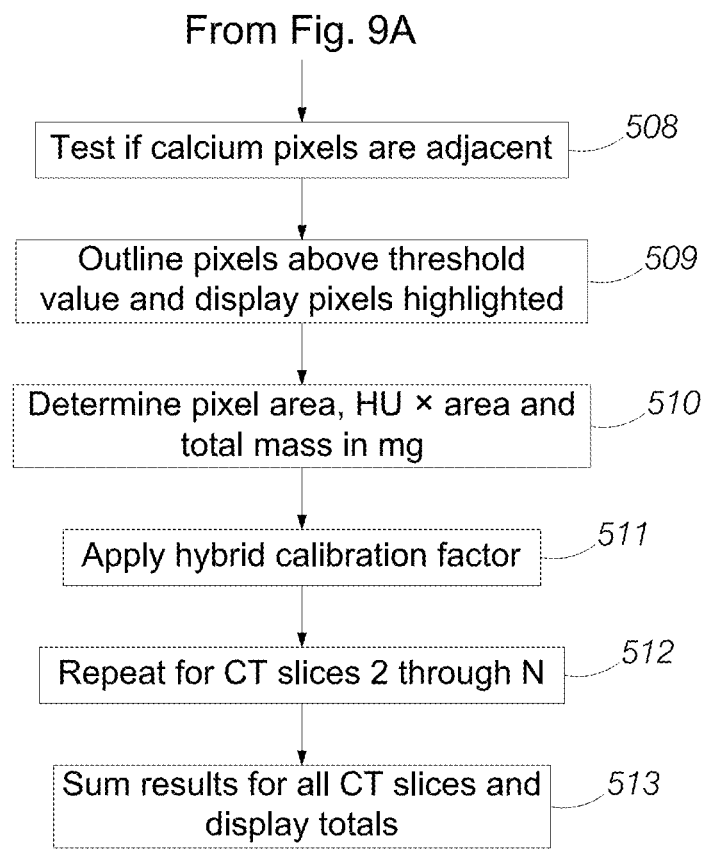

In FIG. 9, comprising FIGS. 9A and 9B, the software first automatically locates the calibration phantom and places ROIs in the phantom sample in a step 500. The phantom calibration equation is determined by regression analysis in a step 501. The slope and intercept of this regression equation may or may not later be combined with the in vivo blood sample calibration to obtain a hybrid calibration equation. The regression intercept of the calibration phantom will be re-calibrated by shifting its value based on the blood pool calibrated pixel values such that all CT slices will produce the same calibrated blood CT values. This is an improvement of the phantom calibration method to allow a second-order correction determined from a homogeneous tissue within the body of a known density (blood), which will further improve accuracy and precision. Calibration is next applied to each CT image or to a cropped section of that image 502. The location of a vertebral body is next found automatically. The exterior contours of the vertebral body are next identified in a step 503. This can be accomplished with relatively simple edge detection algorithms since the tissue density contrast is larger between the cortical bone and the surrounding soft tissue. The three-dimensional coordinates of the exterior cortical bone contours are recorded in a step 504. The algorithm then creates a series of spatial shifts one pixel width and performs a search along that shifted contour.

Figure 11:
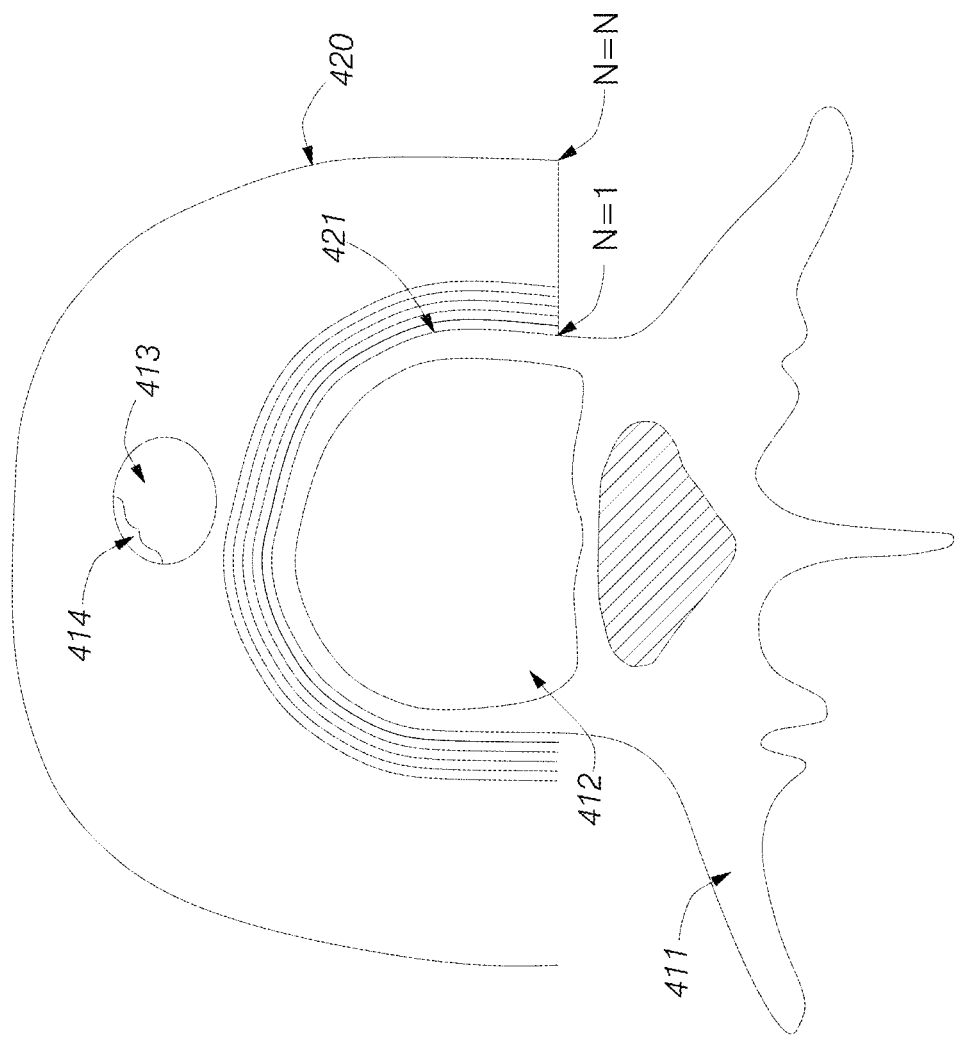
FIG. 11 illustrates a depiction of the procedure used in certain embodiments to automatically locate the aorta.

In FIG. 11, the search procedure is shown in more detail. The first contour N=1 is directly adjacent and follows the vertebral contour 421. Pixels located on this contour above the threshold are identified and located. The contour is next shifted one pixel to N=2, and the search is repeated on this contour in a step 505. This procedure is repeated N times to a final contour 420. This creates a search region sufficiently large to insure the aorta will be included in a step 506. In a step 507, the maximum contour may be sized proportionately to the cross-sectional area of the image to account for differences in patient sizes. Since the aorta is positioned anterior to the vertebral body and is surrounded by soft tissue in a relatively large body cavity, ribs and bones or other distracting structures are not present to confuse the search algorithm.

Using shape and density constraints, the aorta images can usually be located automatically. The use of the hybrid calibration aids the search by defining in quantitative and reproducible units the edge of the aorta. The final region of search calcifications is located by threshold analysis. The threshold is preferably calibrated to the calibration equation.

When pixels are located that contain calcium, as defined above the threshold value, the pixels are tested to see if neighboring pixels both in that image and in adjacent images in the stack contain calcium in step 508. In some cases, a calcification will be arbitrarily defined as having three or more pixels before it is scored as calcium. Single pixels, unless of very high density, may be noise and are not scored. The pixels which meet these detection criteria are highlighted in a step 509 and may be displayed on a reformatted or axial image for operator review. The volume and the mass of a calcification may be calculated in a step 510. A further calibration using the hybrid calibration equation may be applied here in a step 511 or the calibration may have already been applied earlier in the procedure. As described above, FIG. 5 shows a histogram of the voxels in a ROI containing blood and heart tissue. A similar histogram peak, although with greater noise, will be obtained from a ROI of the abdominal aorta.

In a step 512, the search and quantification step is repeated N times to analyze all CT slices. The results for each slice are summed and presented as a total calcium score or total calcium mass in step 513.

Figure 12:
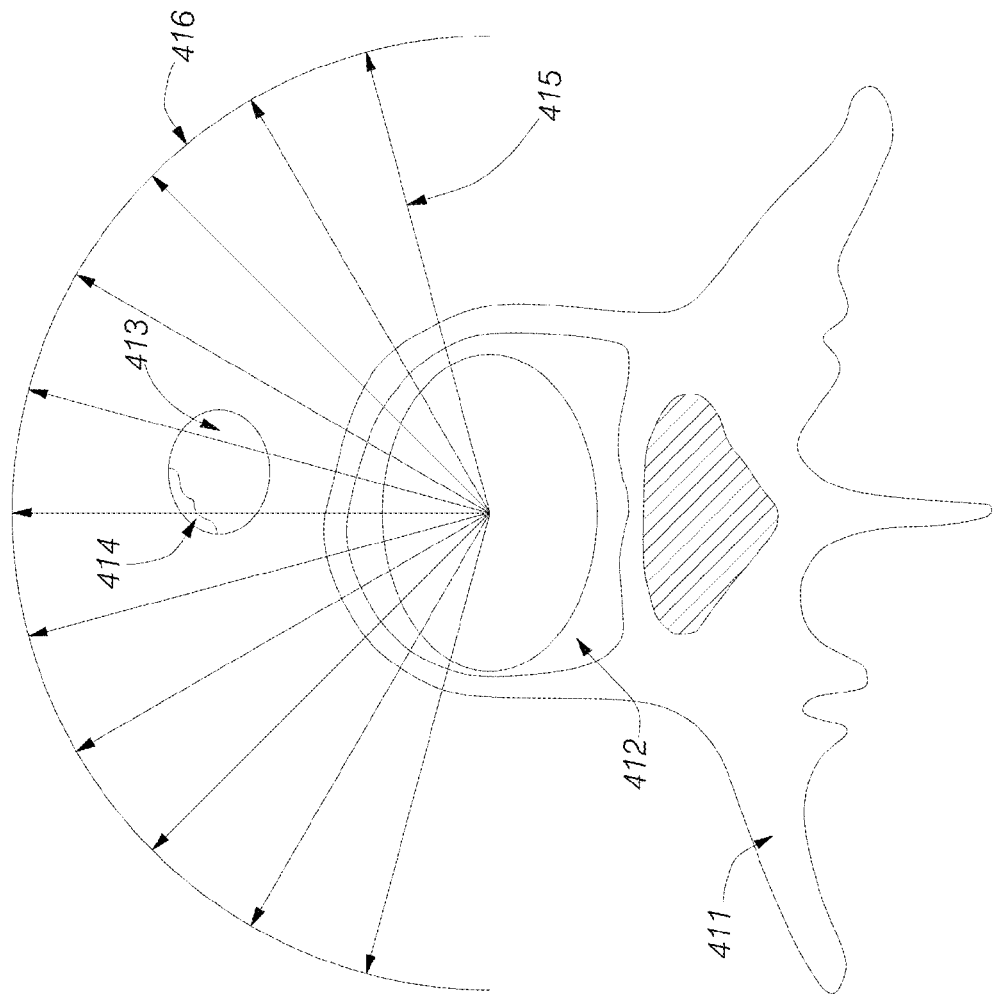
FIG. 12 illustrates a depiction of the scan procedure used in certain embodiments to automatically locate the aorta and aortic calcium.

In another method to automatically locate and quantify aortic calcium, a different search algorithm is used as illustrated in FIG. 12.

Figure 13A:
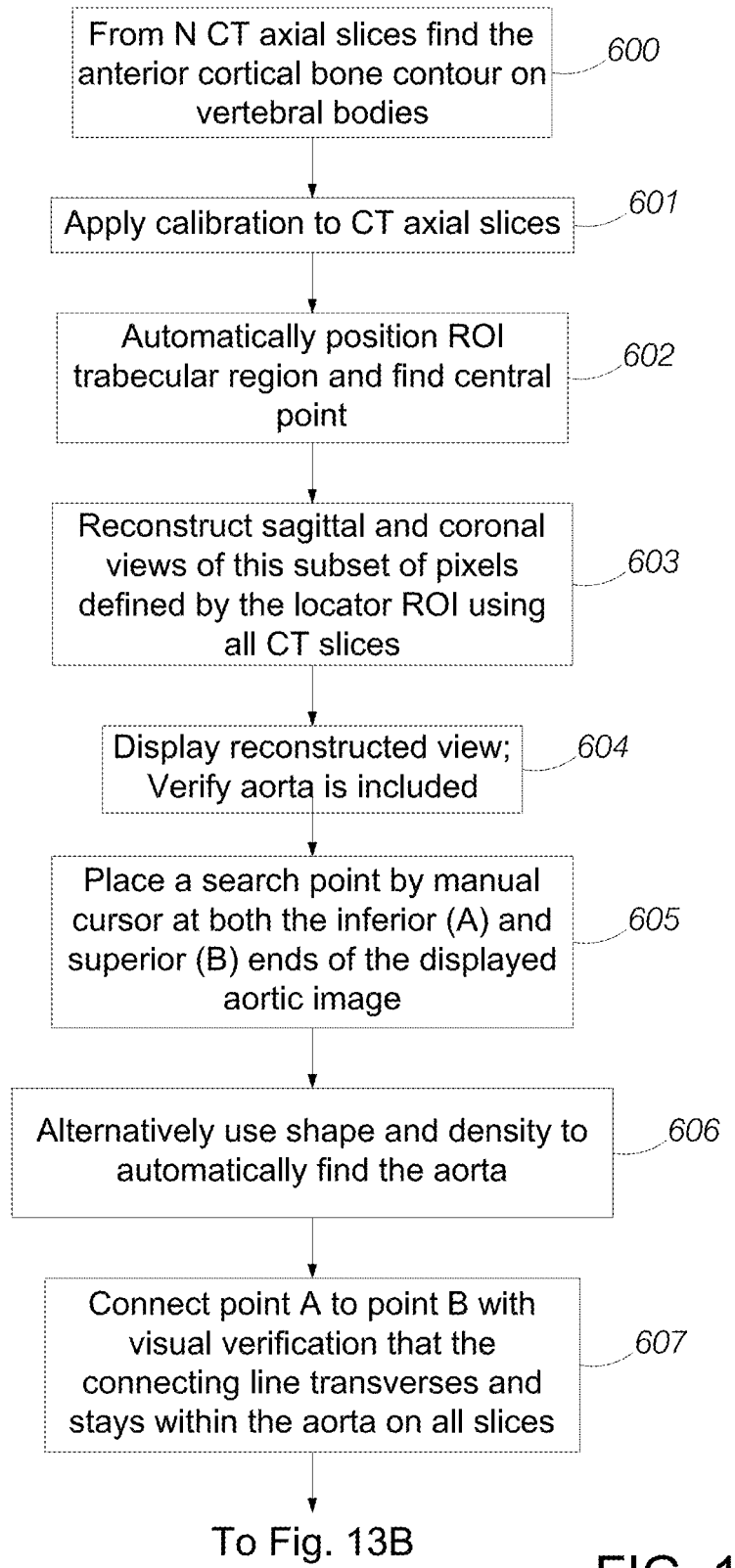
FIGS. 13A and 13B illustrate a flow diagram of another embodiment for a method for automatically locating and quantifying aortic calcium.
Figure 13B:
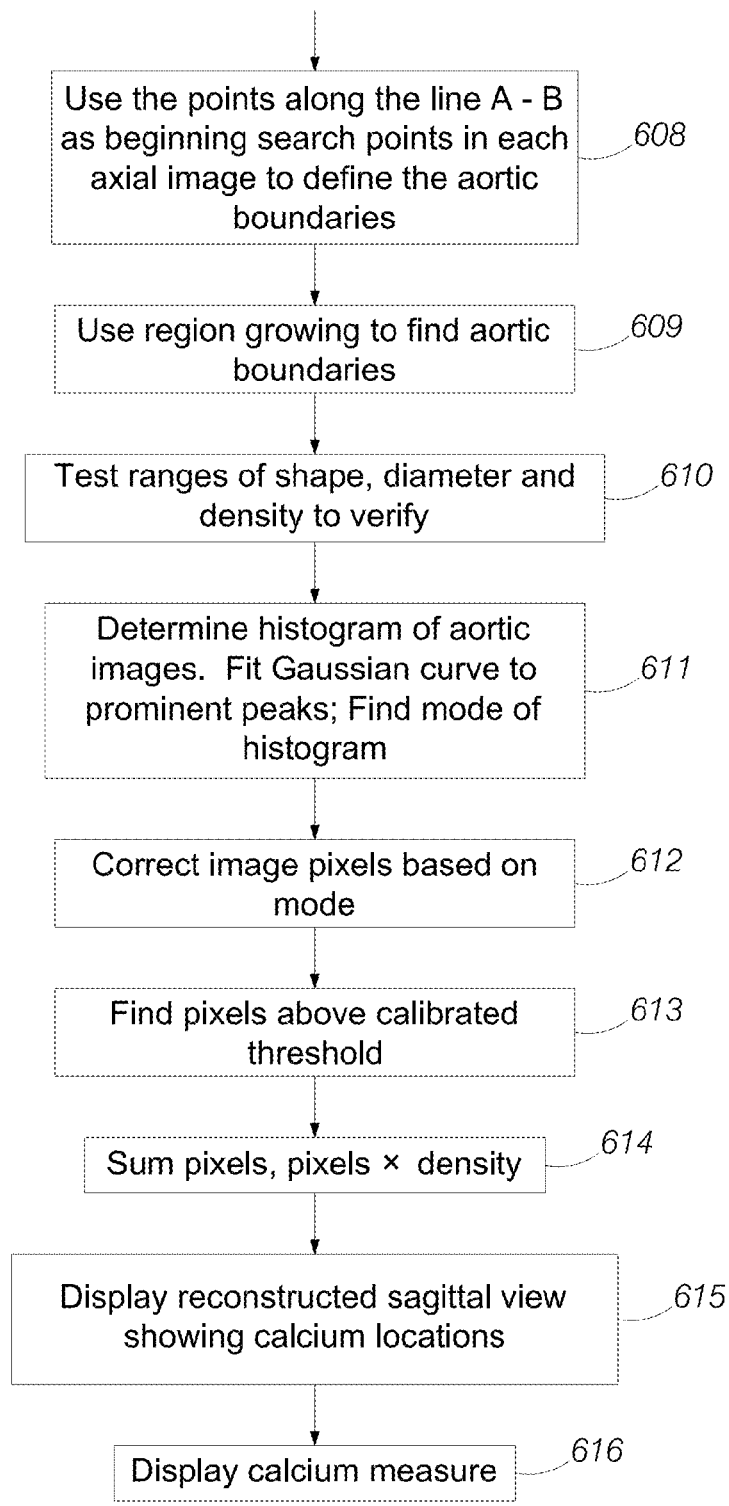

In FIG. 12, the calibration phantom and vertebral body are automatically located by known methods. An elliptical ROI is located automatically with the trabecular region of the vertebral body in a step 602 in FIG. 13, comprising FIGS. 13A and 13B. FIG. 12 shows a depiction of a vertebral body and aorta showing the search lines of the second search algorithm. The trabecular region 412 of the bone is indicated. An elliptical ROI is located within the trabecular region and the center of the ROI forms the initial point for a fan search pattern 416. The search pattern has a 180° angle and extends a distance X from the vertebral contour 415, which insures the aorta 413 is included in the final search region. Once the search region is defined 416, the software searches the region by threshold analysis to locate the aorta and aortic calcification as discussed above and as shown in FIG. 9.

Figure 14:
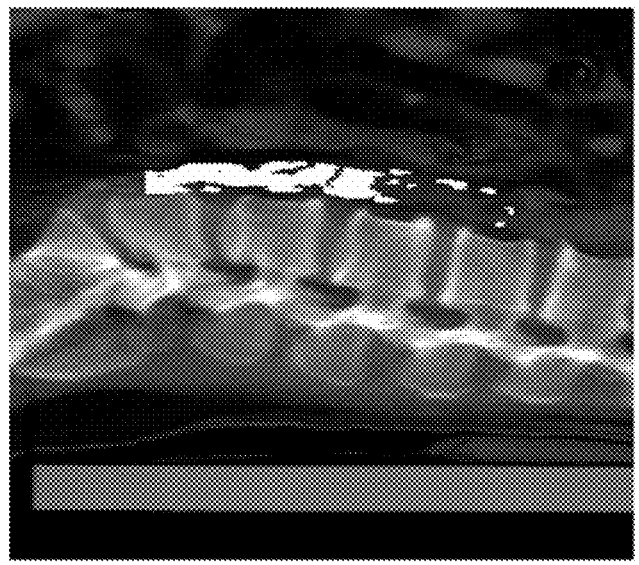
FIG. 14 illustrates a depiction of a sagittal view of a region of the aorta reconstructed from cropped images.

Another embodiment of the methods to automatically detect and quantify aortic calcifications can be understood from FIG. 13 in connection with FIG. 14.

Images from N CT slices of the body containing a larger artery may be calibrated using a reference calibration phantom. Alternatively, with less accuracy, the algorithm will operate without calibration. The artery may be the abdominal aorta. The algorithm finds the vertebral body and anterior cortical bone contour in a step 600. The calibration may be applied in a step 601. In a step 602, the vertebral region with an auto ROI can be used as a beginning point to position a locator search region.

Although FIG. 12 shows a fan beam search region, preferably this region will be extended and cropped to form a rectangular locator ROI which includes the aorta. The locator ROI may or may not include the vertebral body or a portion of the vertebral body.

When the locator search region is automatically located on all axial images, these regions are reformatted into preferably sagittal images. If no part of the vertebral body is included, the coronal reformation may also be used.

The sagittal view is displayed in a step 604 so the operator can verify that the aorta is included. The axial images have been cropped to exclude most of the body, leaving only a relatively thin section of tissue defined by the locator regions. This provides high contrast in the sagittal image to allow visualization of the aorta and calcifications. The operator can next place a search point to define the inferior and superior extent of the aorta in a step 605. Alternatively, the software may use shape and density constraints to locate the aorta automatically in a step 606. The software next connects a point A and a point B and displays the line AB overlaid on the sagittal image. The operator verifies the location of the line and verifies that the line intersects the aorta on all slices in a step 607. The software uses the intersection of the line AB and each axial slice at the intersection to define a search seed point that lies within the aorta in a step 608. Region growing techniques are used to define the aorta and its boundary in a step 609. Calibrated edges are beneficial to improve reproducibility on repeat scans. Sanity checks are performed on the results by comparing expected shapes, diameters and density ranges to those measured on the aorta in a step 610.

In a modification to this technique, the abdominal aorta is located semi-automatically from axial CT images and sagittal reformatted images. The operator applies cursor marks "within" the aortic image on CT slices with a search point. Preferably the first superior image is marked by cursor point within the aortic image, then marked again after the bifurcation on the aorta with two more search points.

Reconstructed sagittal and coronal views of a subset of pixels are defined by the locator box using all CT slices. Contrast enhances the resulting image to display arterial outer margins. A search point is placed by manual cursor at both the inferior (A) and superior (B) ends of the displayed aortic image. The point A is connected to the point B with visual verification that the connecting line transverses and stays within the aorta on all slices. Points along the line AB are used as beginning search points in each axial image to define the aortic boundaries by region growing techniques.

Histogram analysis is performed on the aortic regions with Gaussian curve fits in a step 611. A calibration correction may be applied to pixels in the locator region using the histogram mode and the known blood density in a step 612. Pixels above a set threshold are detected in a step 613 and are summed to provide calcium area or calcium mass in a step 614. The sagittal reformed images may be displayed with the detected calcifications shown on the view in a step 615. This aids in the diagnostic report and provides a quick visual indication of calcium location in the aorta. The final total calcium measure is recorded and displayed in a final report in a step 616.

Although described above in connection with particular embodiments of the present invention, it should be understood the descriptions of the embodiments are illustrative of the invention and are not intended to be limiting. Various modifications and applications may occur to those skilled in the art without departing from the true spirit and scope of the invention as defined in the appended claims.

What is claimed is:

1. An automatic method to measure coronary plaque in a subject using x-ray computed tomography (CT) by acquiring a volumetric set of CT images containing voxels representing x-ray attenuation of the subject, the method comprising:
automatically identifying a three-dimensional (3-D) region of interest (ROI) volume which includes at least a portion of the image of the heart of the subject;
determining a 3-D coordinate system within the 3-D ROI volume;
automatically analyzing the 3-D ROI volume to identify voxels in the volume which satisfy defined criteria;
automatically identifying a location of at least one plaque in one coronary artery within the ROI volume using the identified voxels; and
automatically determining a measure of at least one plaque of at least a portion of one coronary artery in the volume.

2. The method as defined in claim 1, wherein the automatically identified 3-D ROI contains substantially all of the heart and can be adjusted by operator interaction.

3. The method as defined in claim 1, wherein the 3-D ROI volume is placed automatically.

4. The method as defined in claim 1, wherein the plaque represents calcium densities.

5. The method as defined in claim 1, wherein the plaque represents soft plaque with densities less than blood.

6. The method as defined in claim 1, wherein the measure is the mass of calcium in the plaques.

7. The method as defined in claim 1, wherein the measure is the volume of soft plaque.

8. The method as defined in claim 1, wherein the defined criteria include a minimum of connected voxels and one or more thresholds of voxel densities.

9. The method as defined in claim 8, wherein the defined criteria may include different numbers of connected voxels defined by sides, edges, or corners connected in 3-D space.

10. The method as defined in claim 8, wherein the thresholds are calculated using the measured full-width-at-half maximum (FWHM) of the measured histograms of the voxel intensities.

11. The method as defined in claim 8, wherein the thresholds are calculated using a measure of the intensity of the blood or the muscle or the blood and the muscle of the subject.

12. The method as defined in claim 1, wherein the plaque is soft plaque that represents atherosclerotic plaque, the soft plaque having calculated thresholds less than the density of the blood or the blood and the muscle.

13. A method to measure coronary calcium in a living subject using x-ray computed tomography (CT) by acquiring a volumetric set of CT images containing voxels representing x-ray attenuation of the subject, the method, comprising:
identifying a three-dimensional (3-D) image of the heart;
identifying the location of at least one coronary artery;
automatically analyzing the 3-D image of the heart to identify voxels above one or more threshold values;
automatically analyzing the identified voxels to determine which voxels satisfy a prior set of connectivity criteria; and
automatically determining the calcium content of at least a portion of the coronary artery.

14. The method as defined in claim 13, wherein identifying of the location of at least one artery is determined without operator interaction.

15. A method to measure calcium in coronary arteries of the human body using computed tomography (CT) by acquiring CT images containing voxels representative of x-ray attenuation in the body, the method comprising:
identifying the location of a region containing at least one artery automatically;
identifying calcium within the artery automatically; and
quantifying the calcium without operator interaction.

16. A system to detect and measure plaque in at least one artery of a living subject using x-ray computed tomography images, the system comprising:
means for locating a position of the artery on at least one image;
means for identifying three-dimensional (3-D) regions of interest (ROIs) which include the position of the artery without operator interaction;
means for locating plaque within the artery without operator interaction;
means for automatically locating fat, bone or fat and bone not attributable to the plaque; and
means for quantifying the plaque within the 3-D ROIs not attributed to fat or bone.

17. The system as defined in claim 16, wherein the bone is the sternum.

18. The system as defined in claim 16, wherein the means for locating plaque within the artery further comprises:
means for identifying image elements within the region-of-interest with HU intensities below one or more lower threshold values or above one more upper threshold values; and
means for identifying image elements which are spatially connected to other image elements and constitute a minimum volume.

19. A calcium scoring method of a subject using x-ray computed tomography (CT) by acquiring a plurality of images containing image elements representing x-ray attenuation of the subject, the method comprising:
automatically determining an outline of a body region with a field of the image containing tissue;
automatically removing bone equivalent image elements located within the field;
automatically detecting outlines of arteries contained within the field;
automatically scoring calcium in the CT image with the bone equivalent image elements removed; and
displaying the arterial calcium scores determined from the field with detected artery outlines while excluding calcium from bone equivalent image elements.

20. The calcium scoring method as defined in claim 19, wherein the bone equivalent image elements are removed using connectivity equations.

21. The calcium scoring method as defined in claim 19, wherein the detected arteries are determined using an edge detection algorithm.

22. The calcium scoring method as defined in claim 19, wherein the field is calibrated using readings of blood/muscle tissue.

* * * * *